United States Patent
Mehta et al.

(10) Patent No.: US 6,627,438 B2
(45) Date of Patent: Sep. 30, 2003

(54) DIRECT EXPRESSION OF PEPTIDES INTO CULTURE MEDIA

(75) Inventors: Nozer M. Mehta, Randolph, NJ (US); Angelo P. Consalvo, Monroe, NY (US); Martha V. L. Ray, Nutley, NJ (US); Christopher P. Meenan, Lincoln Park, NJ (US)

(73) Assignee: Unigene Laboratories Inc., Fairfield, NJ (US)

( * ) Notice: Subject to any disclaimer, the term of this patent is extended or adjusted under 35 U.S.C. 154(b) by 65 days.

(21) Appl. No.: 09/780,878

(22) Filed: Feb. 9, 2001

(65) Prior Publication Data

US 2001/0055789 A1 Dec. 27, 2001

Related U.S. Application Data

(62) Division of application No. 09/500,009, filed on Feb. 8, 2000, now Pat. No. 6,210,925, which is a division of application No. 09/060,765, filed on Apr. 15, 1998, now Pat. No. 6,103,495.
(60) Provisional application No. 60/043,700, filed on Apr. 16, 1997.

(51) Int. Cl.$^7$ .................. C12P 21/06; C12N 15/63; C12N 1/12; A61K 38/24; A23J 1/00
(52) U.S. Cl. .................. 435/320.1; 435/252.3; 435/69.4; 435/252.33; 435/69.1; 530/399; 530/300; 530/412; 530/416; 536/23.1; 536/24.1
(58) Field of Search .................. 435/320.1, 252.3, 435/69.4, 252.33, 69.1; 530/399, 300, 412, 416; 536/23.1, 24.1

(56) References Cited

U.S. PATENT DOCUMENTS

| | | | |
|---|---|---|---|
| 4,595,658 A | 6/1986 | Zinder et al. | 435/68 |
| 4,620,948 A | 11/1986 | Builder et al. | 530/419 |
| 4,708,934 A | 11/1987 | Gilligan et al. | 435/68 |
| 4,757,013 A | 7/1988 | Inouye et al. | 435/172.3 |
| 5,089,406 A | 2/1992 | Williams et al. | 435/172.3 |
| 5,223,407 A | 6/1993 | Wong et al. | 435/69.1 |
| 5,240,831 A | 8/1993 | Barnes | 435/69.1 |
| 5,332,664 A | 7/1994 | Craig et al. | 435/69.4 |
| 5,547,862 A | 8/1996 | Meador et al. | 435/91.3 |
| 5,589,364 A | 12/1996 | Williams et al. | 435/69.7 |
| 5,747,281 A | 5/1998 | Shuler et al. | 435/69.1 |

FOREIGN PATENT DOCUMENTS

| | | |
|---|---|---|
| EP | 177343 | 10/1985 |
| EP | 308067 | 8/1988 |
| EP | 382403 | 2/1990 |

OTHER PUBLICATIONS

Stark, MJ, Multicopy expression vectors carrying the lac repressor gene for regulated high-level expression of genes in *Escherichia coli*, 1987, Gene, vol. 51, pp. 255–267.*

Ray et al. *Bio/Technology*, 11:64–70 (1993).
Watson, *Nucleic Acids Research*, 12(13):5145–5164.
Hsiung et al., *Biotechnology*, 4:991–995 (1986).
Vaara, *Microbiological Reviews*, 56:395–411 (1992).
Kaderbhai et al., *Biotech. Appl. Biochem.*, 25:53–61 (1997).
Nagahari et al., *EMBO J.*, 4(13A):3589–3592 (1987).
Miller et al., *ABB*, 298:380–388 (1992).
Mizuno et al., *BBRC*, 148(2):546–552 (1987).
Lin Ying et al., *Chin. Med. Sci. J.*, 11(1):204–208 (1996).
Costello et al., *Journal of Bacteriology*, 178(6):1623–1630 (1996).
Fujiyama et al., *FEMS Microbiology Letters*, 126:19–24 (1995).
Hasan et al., *Gene*, 56:145–151 (1987).
Ito et al., *Gene*, 118:87–91 (1992).
Murakami et al., *Applied Microbiology and Biotechnology*, 619–623 (1989).
Nakamura et al., *EMBO J.*, 1(6):771–775 (1982).
Perez et al., *Bio/Technology*, 12:178–180 (1994).
Perez et al., *Journal of Biotechnology*, 49:245–247 (1996).
Yu et al., *Biotechnology Letters*, 13(5):311–316 (1991).
Dykxhoorn et al., *Gene*, 177:133–136 (1996).
Koke et al., *Protein Expression & Purification*, 2:51–58 (1991).
Hasan et al., *Gene*, 56:145–151 (1987).
Ying et al., *Clin. Med. Sci. J.*, 11(4):204–208 (1996).
Ray et al., *Bio/technology*, 11:64–70 (1993).
Medline Abstract PMID: 1337577 (Asselbergs, et al., *Mol. Biol. Rep.*, 17(1):61–70 (1992)).
Medline Abstract PMID: 1847347 (Morales, et al.) (1991).
Medline Abstract PMID: 7990813 (Slobodkina, et al.) (1994).
*Protein Engineering, Principles and Practice*, Eds Cleland and Craik (1996), Chapter 4.
Computer Database Printout dated Jun. 18, 1999 from Australian Search Report.

* cited by examiner

Primary Examiner—Christopher S. F. Low
Assistant Examiner—Holly Schnizer
(74) Attorney, Agent, or Firm—Ostrolenk, Faber, Gerb & Soffen, LLP

(57) ABSTRACT

Expression systems are disclosed for the direct expression of peptide products into the culture media where genetically engineered host cells are grown. High yield was achieved with novel vectors, a special selection of hosts, and/or fermentation processes which include careful control of cell growth rate, and use of an inducer during growth phase. Special vectors are provided which include control regions having multiple promoters linked operably with coding regions encoding a signal peptide upstream from a coding region encoding the peptide of interest. Multiple transcription cassettes are also used to increase yield. The production of amidated peptides using the expression systems is also disclosed.

2 Claims, 27 Drawing Sheets

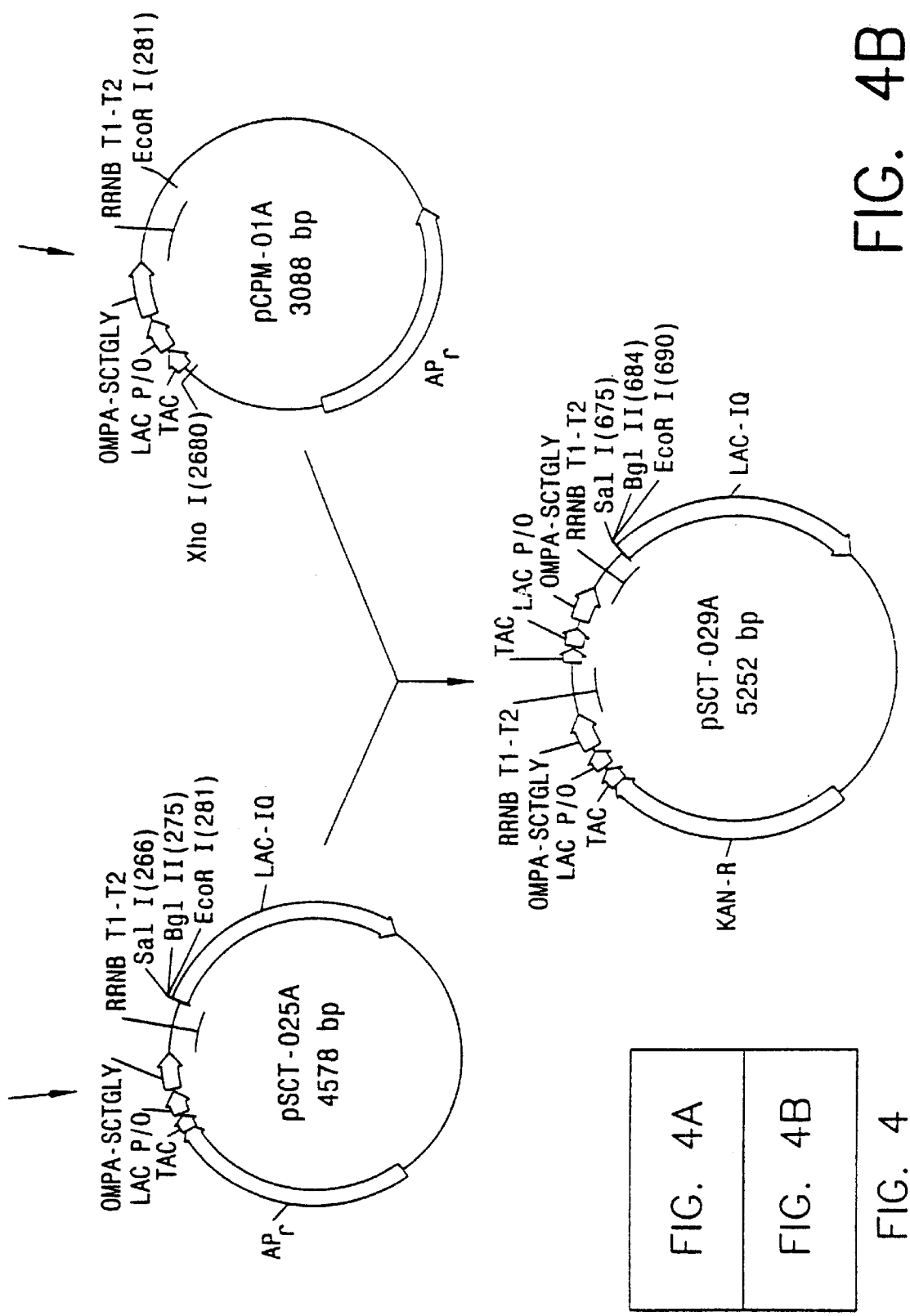

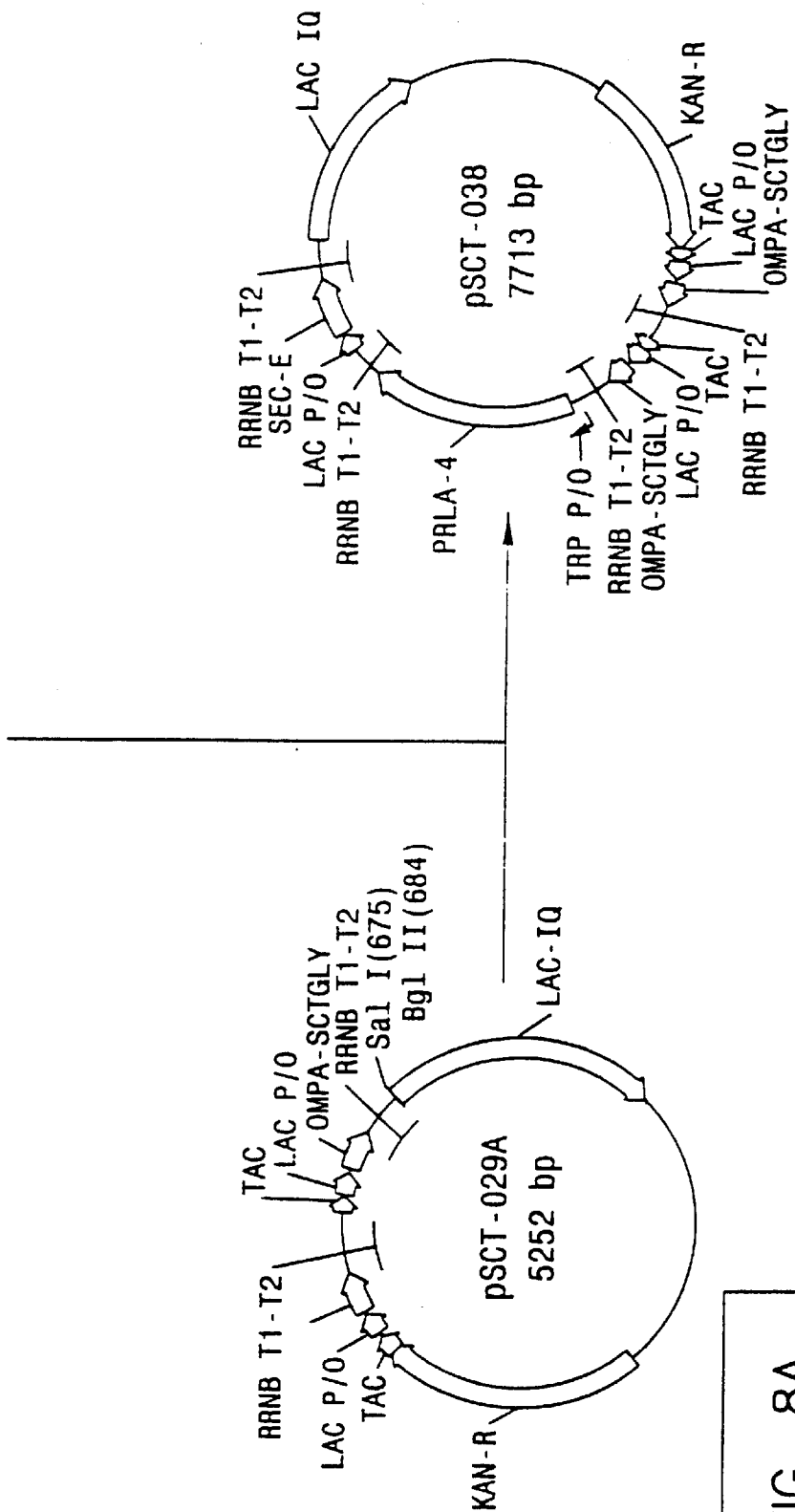

DIRECT EXPRESSION OF PEPTIDES INTO CULTURE MEDIA

RELATED APPLICATION

This is a division of application Ser. No. 09/500,009, filed Feb. 8, 2000, now U.S. Pat. No. 6,210,925, which is a division of application Ser. No. 09/060,765, filed Apr. 15, 1998, now U.S. Pat. No. 6,103,495, which claims priority of U.S. Provisional Application No. 60/043,700, filed Apr. 16, 1997.

FIELD OF THE INVENTION

The present invention relates to direct expression of a peptide product into the culture medium of genetically engineered host cells expressing the peptide product. More particularly, the invention relates to expression vectors, host cells and/or fermentation methods for producing a peptide product that is excreted outside the host into the culture medium in high yield. In some embodiments, the invention relates to direct expression of a peptide product having C-terminal glycine which is thereafter converted to an amidated peptide having an amino group in place of said glycine.

DESCRIPTION OF THE RELATED ART

Various techniques exist for recombinant production of peptide products, i.e. any compound whose molecular structure includes a plurality of amino acids linked by a peptide bond. A problem when the foreign peptide product is small is that it is often readily degradable by endogenous proteases in the cytoplasm or periplasm of the host cell that was used to express the peptide. Other problems include achieving sufficient yield, and recovering the peptide in relatively pure form without altering its tertiary structure (which can undesirably diminish its ability to perform its basic function). To overcome the problem of small size, the prior art has frequently expressed the peptide product of interest as a fusion protein with another (usually larger) peptide and accumulated this fusion protein in the cytoplasm. The other peptide may serve several functions, for example to protect the peptide of interest from exposure to proteases present in the cytoplasm of the host. One such expression system is described in Ray et al., *Bio/Technology*, Vol. 11, pages 64–70, (1993).

However, the isolation of the peptide product using such technology requires cleavage of the fusion protein and purification from all the peptides normally present in the cytoplasm of the host. This may necessitate a number of other steps that can diminish the overall efficiency of the process. For example, where a prior art fusion protein is accumulated in the cytoplasm, the cells must usually be harvested and lysed, and the cell debris removed in a clarification step. All of this is avoided in accordance with the present invention wherein the peptide product of interest is expressed directly into, and recovered from, the culture media.

In the prior art it is often necessary to use an affinity chromatography step to purify the fusion protein, which must still undergo cleavage to separate the peptide of interest from its fusion partner. For example, in the above-identified *Bio/Technology* article, salmon calcitonin precursor was cleaved from its fusion partner using cyanogen bromide. That cleavage step necessitated still additional steps to protect cysteine sulfhydryl groups at positions 1 and 7 of the salmon calcitonin precursor. Sulfonation was used to provide protecting groups for the cysteines. That in turn altered the tertiary structure of salmon calcitonin precursor requiring subsequent renaturation of the precursor (and of course removal of the protecting groups).

The peptide product of the invention is expressed only with a signal sequence and is not expressed with a large fusion partner. The present invention results in "direct expression". It is expressed initially with a signal region joined to its N-terminal side. However, that signal region is post-translationally cleaved during the secretion of the peptide product into the periplasm of the cell. Thereafter, the peptide product diffuses or is otherwise excreted from the periplasm to the culture medium outside the cell, where it may be recovered in proper tertiary form. It is not linked to any fusion partner whose removal might first require cell lysing denaturation or modification, although in some embodiments of the invention, sulfonation is used to protect cysteine sulfhydryl groups during purification of the peptide product.

Another problem with the prior art's accumulation of the peptide product inside the cell, is that the accumulating product can be toxic to the cell and may therefore limit the amount of fusion protein that can be synthesized. Another problem with this approach is that the larger fusion partner usually constitutes the majority of the yield. For example, 90% of the production yield may be the larger fusion partner, thus resulting in only 10% of the yield pertaining to the peptide of interest. Yet another problem with this approach is that the fusion protein may form insoluble inclusion bodies within the cell, and solubilization of the inclusion bodies followed by cleavage may not yield biologically active peptides.

The prior art attempted to express the peptide together with a signal peptide attached to the N-terminus to direct the desired peptide product to be secreted into the periplasm (see EP 177,343, Genentech Inc.). Several signal peptides have been identified (see Watson, M. Nucleic Acids Research, Vol 12, No.13, pp: 5145–5164). For example, Hsiung et al. (Biotechnology, Vol 4, November 1986, pp: 991–995) used the signal peptide of outer membrane protein A (OmpA) of $E.\ coli$ to direct certain peptides into the periplasm. Most often, peptides secreted to the periplasm frequently tend to stay there with minimal excretion to the medium. An undesirable further step to disrupt or permeabilize the outer membrane may be required to release sufficient amounts of the periplasmic components. Some prior art attempts to excrete peptides from the periplasm to the culture media outside the cell have included compromising the integrity of the outer membrane barrier by having the host simultaneously express the desired peptide product containing a signal peptide along with a lytic peptide protein that causes the outer membrane to become permeable or leaky (U.S. Pat. No. 4,595,658). However, one needs to be careful in the amount of lytic peptide protein production so as to not compromise cellular integrity and kill the cells. Purification of the peptide of interest may also be made more difficult by this technique.

Aside from outer membrane destabilization techniques described above there are less stringent means of permeabilizing the outer membrane of gram negative bacteria. These methods do not necessarily cause destruction of the outer membrane that can lead to lower cell viability. These methods include but are not limited to the use of cationic agents (Martti Vaara., Microbiological Reviews, Vol. 56, pages 395–411 (1992)) and glycine (Kaderbhai et al., Biotech. Appl. Biochem, Vol. 25, pages 53–61 (1997)) Cationic agents permeabilize the outer membrane by interacting with and causing damage to the lipopolysaccharide backbone of the outer membrane. The amount of damage and disruption can be non lethal or lethal depending on the concentration used. Glycine can replace alanine residues in the peptide component of peptidoglycan. Peptidoglycan is one of the structural components of the outer cell wall of gram negative bacteria. Growing E. coli in high concentration of glycine increases the frequency of glycine-alanine replacement resulting in a defective cell wall, thus increasing permeability.

Another prior art method of causing excretion of a desired peptide product involves fusing the product to a carrier protein that is normally excreted into the medium (hemolysin) or an entire protein expressed on the outer membrane (e.g. ompF protein). For example, human β-endorphin can be excreted as a fusion protein by E. coli cells when bound to a fragment of the ompF protein (EMBO J., Vol 4, No. 13A, pp:3589–3592, 1987). Isolation of the desired peptide product is difficult however, because it has to be separated from the carrier peptide, and involves some (though not all) of the drawbacks associated with expression of fusion peptides in the cytoplasm.

Yet another prior art approach genetically alters a host cell to create new strains that have a permeable outer membrane that is relatively incapable of retaining any periplasmic peptides or proteins However, these new strains can be difficult to maintain and may require stringent conditions which adversely affect the yield of the desired peptide product.

Raymond Wong et al. (U.S. Pat. No. 5,223,407) devised yet another approach for excretion of peptide products by making a recombinant DNA construct comprising DNA coding for the heterologous protein coupled in reading frame with DNA coding for an ompA signal peptide and control region comprising a tac promoter. This system reports yields significantly less than those achievable using the present invention.

Although the prior art may permit proteins to be exported from the periplasm to the media, this can result in unhealthy cells which cannot easily be grown to the desirable high densities, thus adversely affecting product yield.

The present invention seeks to produce peptide in high yield with an efficient expression vector, and to provide high yield culturing techniques and other improvements which permits high yield recovery of excreted peptide of interest from the culture media, without overly disrupting the integrity of the cell membrane.

SUMMARY OF THE INVENTION

Accordingly, it is an object of the present invention to have a peptide product accumulate in good yield in the medium in which peptide-producing host cells are growing. This is advantageous because the medium is relatively free of many cellular peptide contaminants.

It is another object of the invention to provide an improved fermentation process for increasing the yield of a peptide product expressed by genetically engineered host cells.

It is another object of the invention to provide genetically engineered host cells that are particularly useful in expressing the novel expression vectors of the invention.

It is another object of the invention to provide a host cell which is particularly suited to the production of salmon calcitonin precursor, regardless of the expression vector utilized for expression of salmon calcitonin.

It is a further object of the invention to provide improved methods for the production of amidated peptides utilizing precursor peptides having C-terminal glycines, which precursors are amaidated following direct expression into the culture medium in accordance with the invention.

In one embodiment, the invention provides an expression vector comprising: (a) a coding region with nucleic acids coding for a peptide product coupled in reading frame 3' of nucleic acids coding for a signal peptide; and (b) a control region linked operably with the coding region, said control region comprising a plurality of promoters and at least one ribosome binding site, wherein at least one of said promoters is tac. Host cells transformed or transfected with the vector are provided, as are methods of direct expression of the peptide product by culturing such host cells.

In another embodiment, the invention provides a host cell transformed with an expression vector which comprises a gene for expressing salmon calcitonin precursor, or calcitonin gene related peptide precursor, said host cell being E. coli strain BLR; and methods of culturing the same to obtain said precursor in the media.

In another embodiment, the invention provides a method of producing an amidated peptide product by producing a precursor having a C-terminal glycine using any of the vectors, hosts, or fermentation processes reported herein; and thereafter converting said glycine to an amino group to produce a peptide amide.

In another embodiment, the invention provides a method for direct expression of a peptide product into a culture medium comprising the steps of: (a) culturing, in said medium, genetically engineered host cells which express said peptide product together with a signal peptide under conditions wherein growth of said host cells is controlled to stay within a range of 0.05 to 0.20 doublings per hour; wherein an inducer is present during some of said period of controlled growth; and (b) recovering said peptide product from the culture medium after intracellular cleavage of the signal peptide.

In another embodiment, glycine is added to the medium during the course of direct expression fermentation, in order to increase the permeability of the outer membrane and enhance excretion of the peptide product.

TAC—Hybrid promoter of tryptophan E and lac operator sequences;

LAC P/O—Region containing lac promoter and lac operator of β galactosidase gene;

LAC-IQ—Gene coding for the lac repressor that binds to operator region of lac promoter and tac promoter. IPTG competes with lac repressor and inhibits binding of lac repressor to operator region of both tac promoter and lac promoter, thus inducing said promoters.

TRP P/O—Promoter operator region of tryptophan E gene;

OMPA-SCTGLY—Gene fusion containing secretory signal sequence of the outer membrane protein A gene and the coding sequence for glycine extended salmon calcitonin (the salmon calcitonin precursor);

SEC-E (also known as "PrlG")—Gene coding for secretion factor E of *E. coli*. It combines with prlA [also known as secy] or prlA-4 to form the inner membrane translocation domain of the sec pathway by which signal sequence containing proteins are translocated from the cytoplasm to the periplasm;

PRLA-4—Mutant allele of prlA gene;

RRNB T1–T2—Tandem transcription terminators 1 and 2 from *E. coli* Ribosomal protein gene; and KAN-R—Kanamycin resistance gene.

Figure 9:
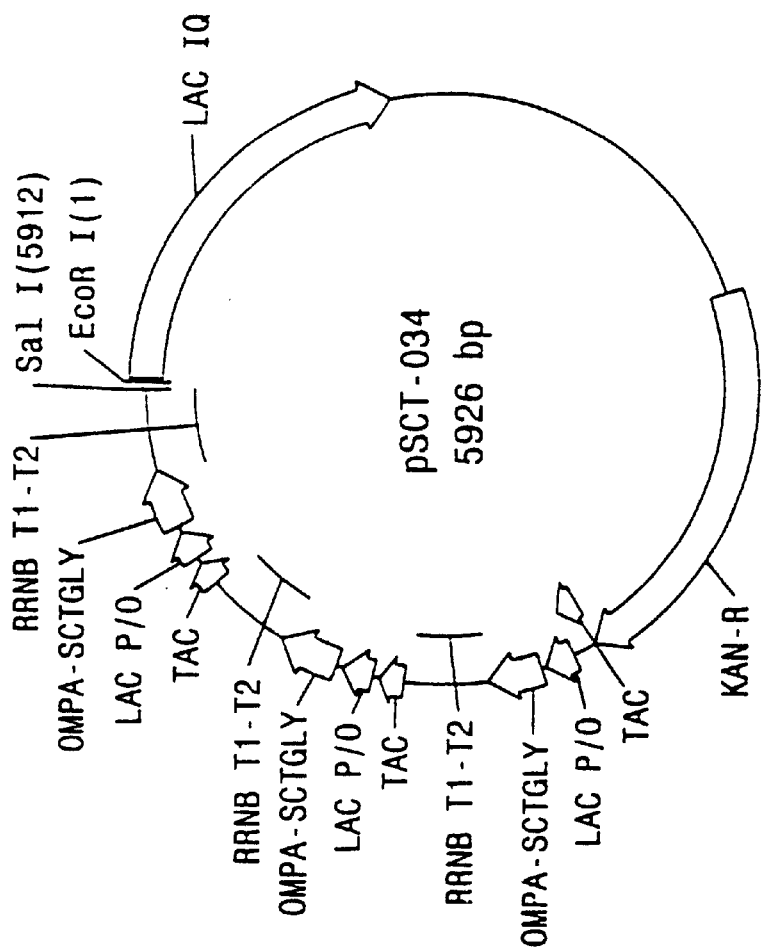

FIG. 9 shows a schematic diagram of the PSCT-034 vector which was used to transform E. coil BLR and produce the trigenic UGL 168 clone.

Figure 10:
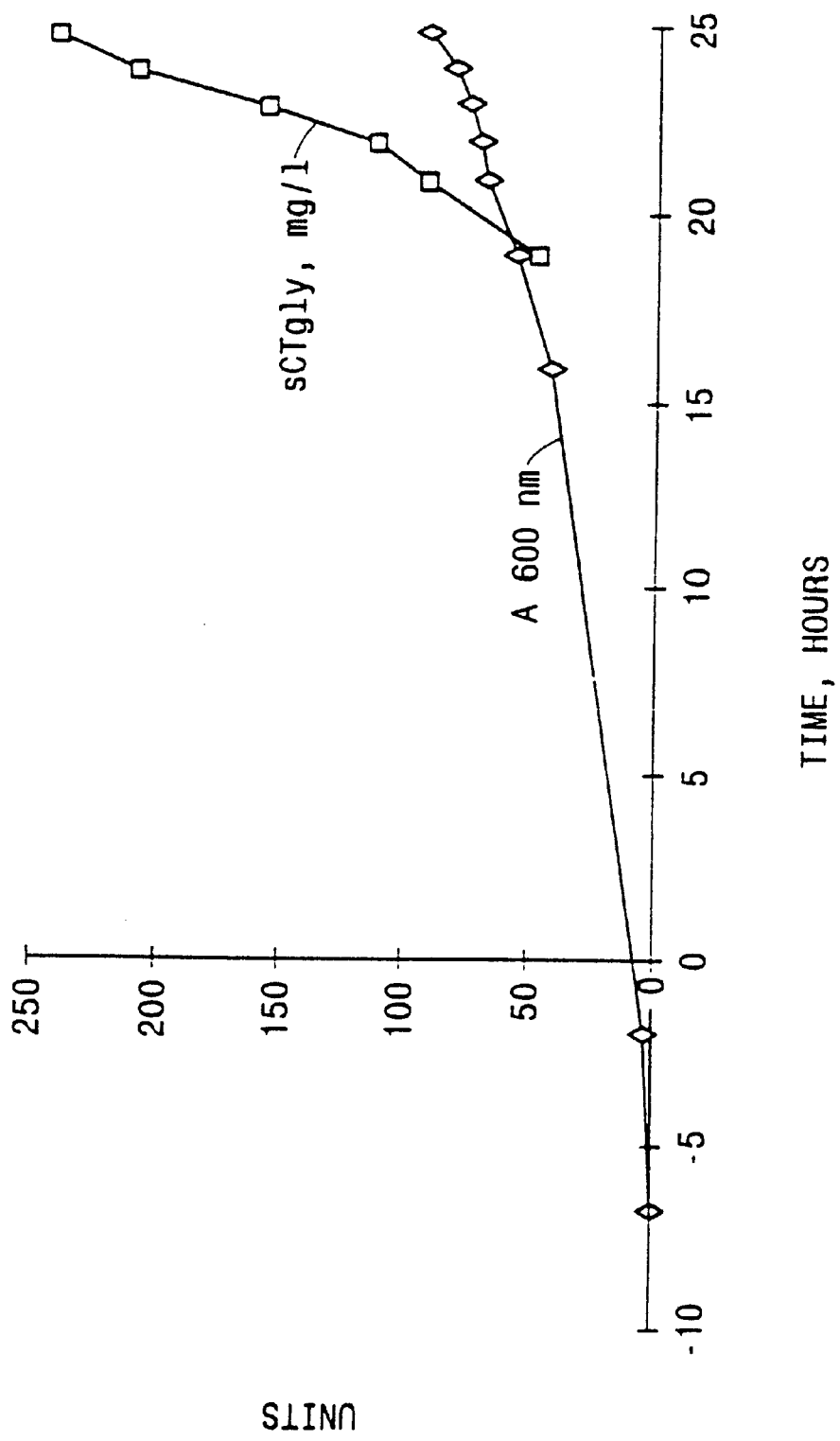

FIG. 10 shows cell growth and sCTgly production of UGL 165 clone (plasmid pSCTO29A in *E. coli* BLR) over time after a typical 1 liter fermentation in the presence of inducer. Cell growth was measured by light absorbance at a wavelength of 600 nm. sCTgly production was reported as mg of sCTgly excreted per liter of incubation medium. Time zero indicates the time at which inducer is first added to the culture medium where host cells of the invention are being cultured. FIG. 10 shows that most of the sCTgly production by UGL 165 occurs between 20 and 25.5 hours after inducer is first added to the culture media where host cells of the invention are being cultured.

Figure 11:
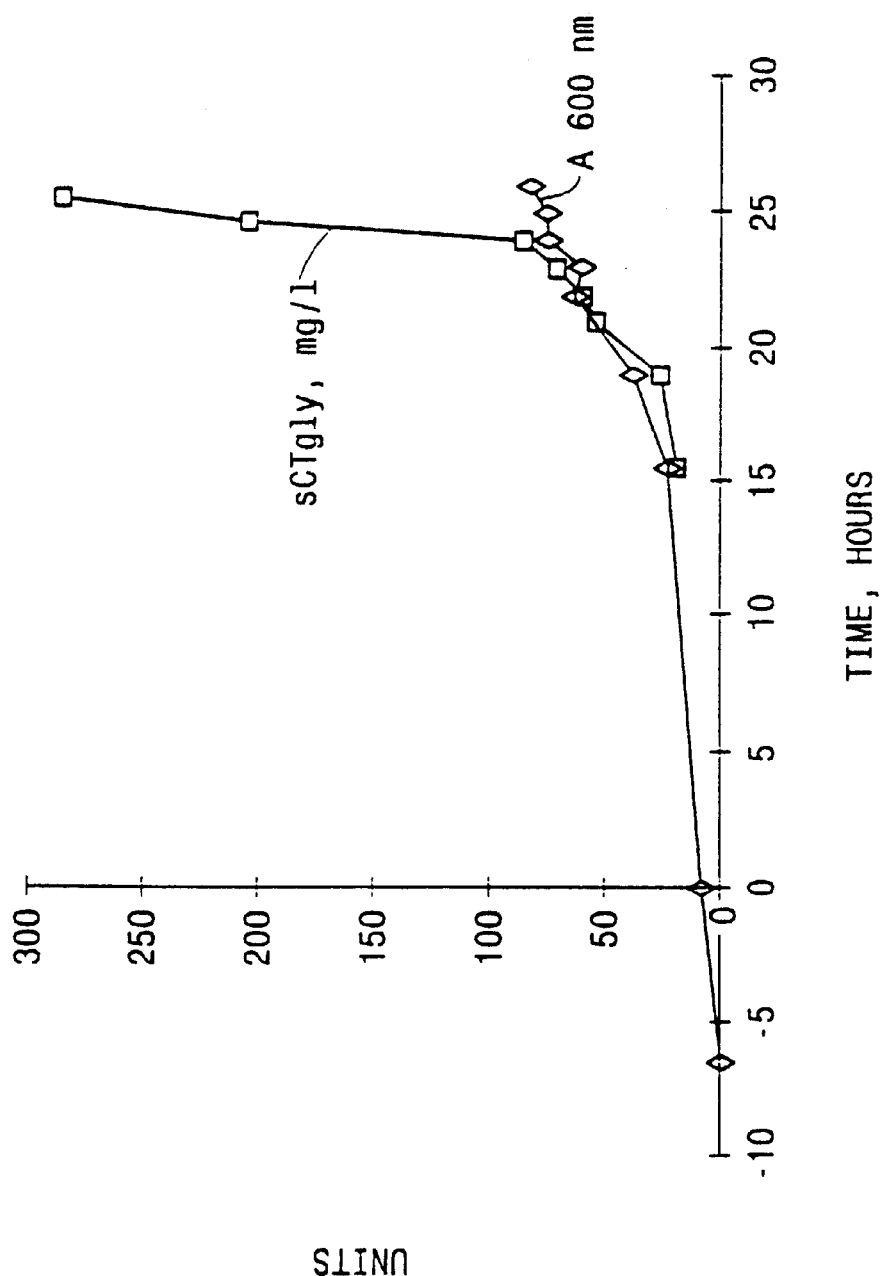

FIG. 11 shows cell growth and sCTgly production of UGL 703 clone (plasmid pSCT 038 in *E. coli* BLR) over time after a typical 1 liter fermentation in the presence of inducer. Cell growth was measured by light absorbance at a wavelength of 600 nm. sCTgly production was reported as mg of sCTgly excreted per liter of incubation medium. Time zero indicates the time at which inducer is first added to the culture medium where host cells of the invention are being cultured. FIG. 11 shows that most of the sCTgly production by UGL 703 occurs between 20 and 26 hours after culture in the presence of inducer.

Figure 12:
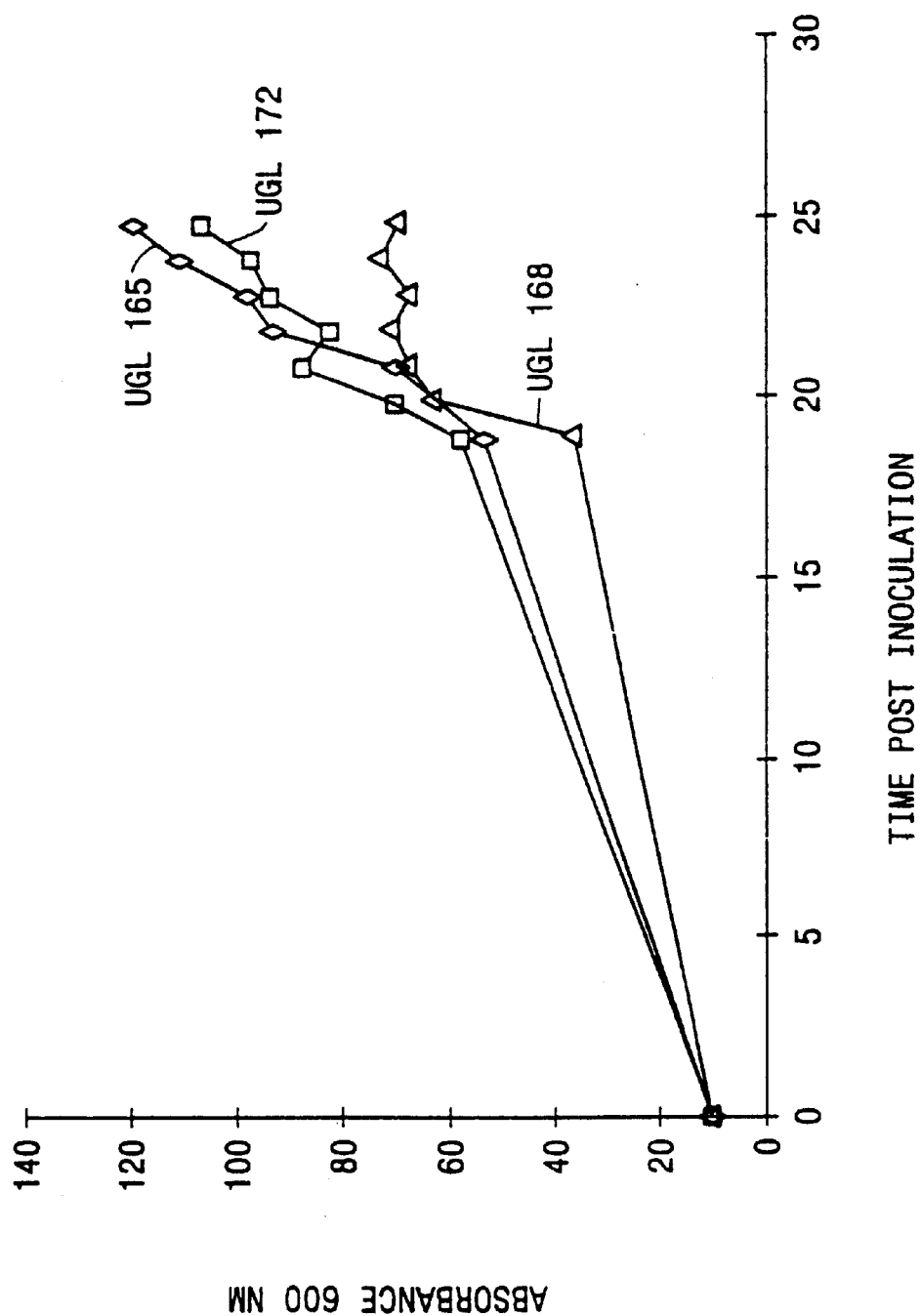

FIG. 12 shows a comparison of the cell growth of UGL 172 clone (plasmid pSCT 025 in *E. coli* BLR), UGL 165 clone and UGL 168 clone (plasmid pSCT 034 in *E. coli* BLR) in a typical 1 liter fermentation over time after incubation in the presence of inducer as measured by absorbance at a wavelength of 600 nm. FIG. 12 shows no significant differences in cell growth rates of UGL 165 and UGL 172 while UGL 168 shows a slight reduction in cell growth rate in this particular experiment.

Figure 13:
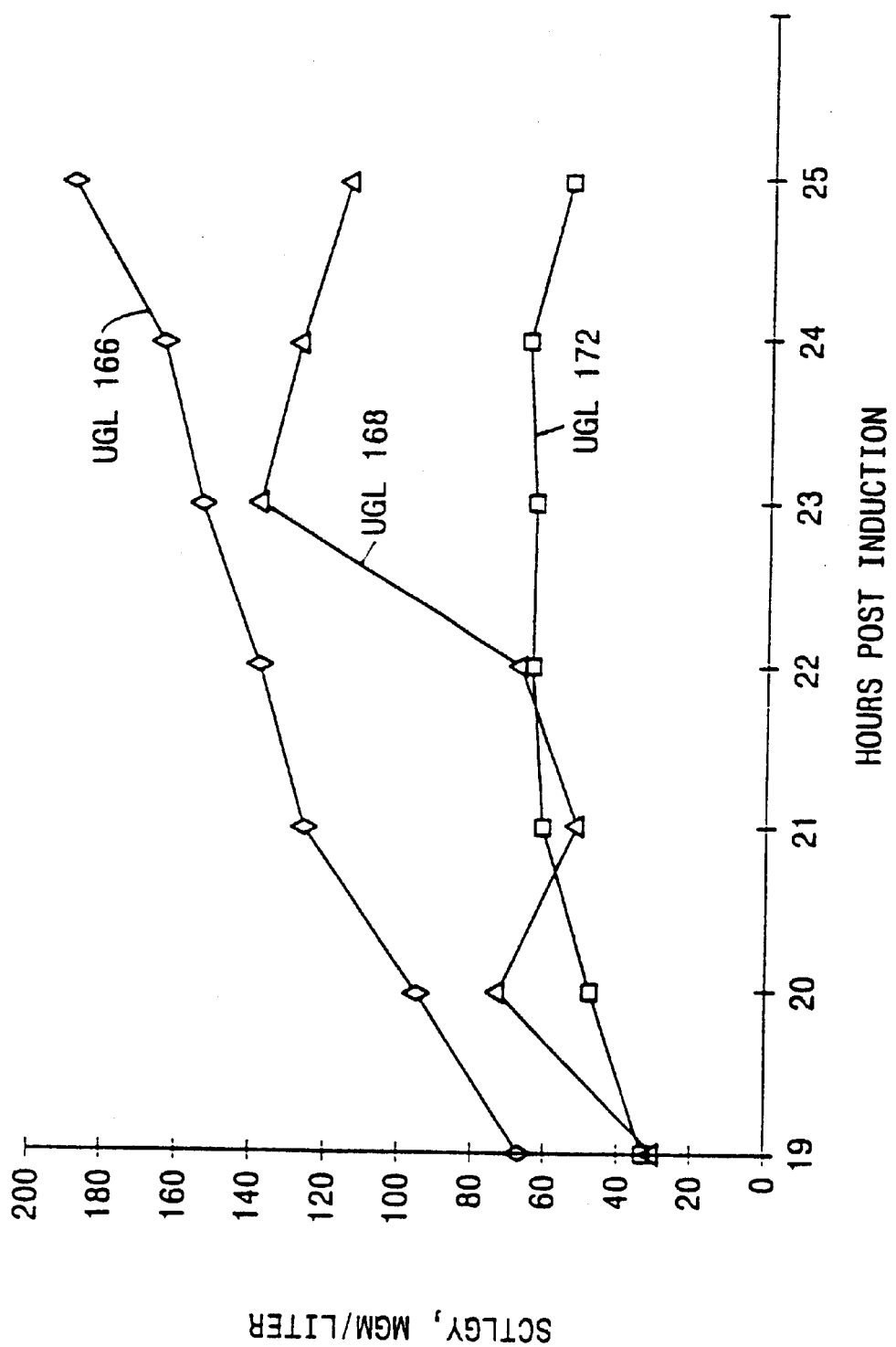

FIG. 13 shows a comparison of sCTgly production by UGL 172 clone, UGL 165 clone and UGL 168 clone over time in a typical 1 liter fermentation after incubation in the presence of inducer reported as mg of sCTgly excreted per liter of incubation medium. FIG. 13 shows that the digenic UGL 165 clone is best suited for production of sCTgly with the trigenic clone being second best over the monogenic UGL 173 clone.

Figure 14A:
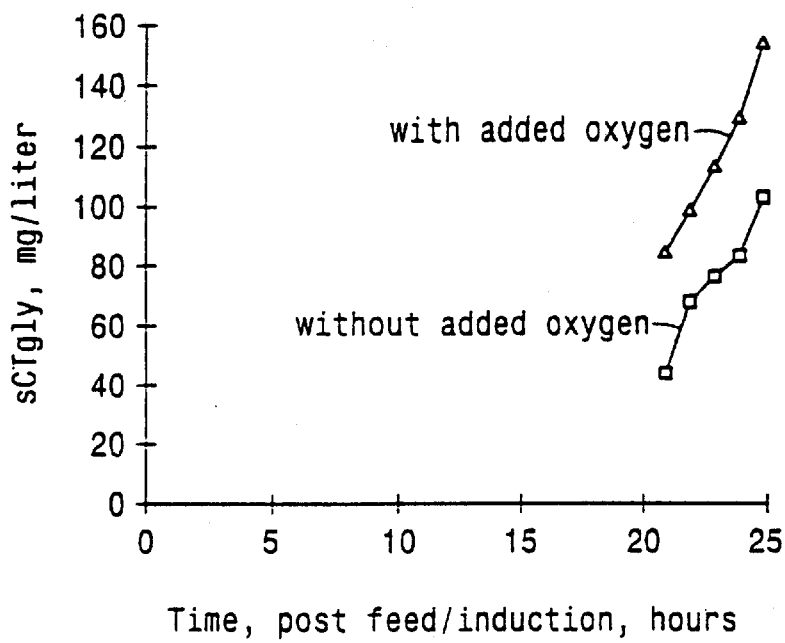
Figure 14B:
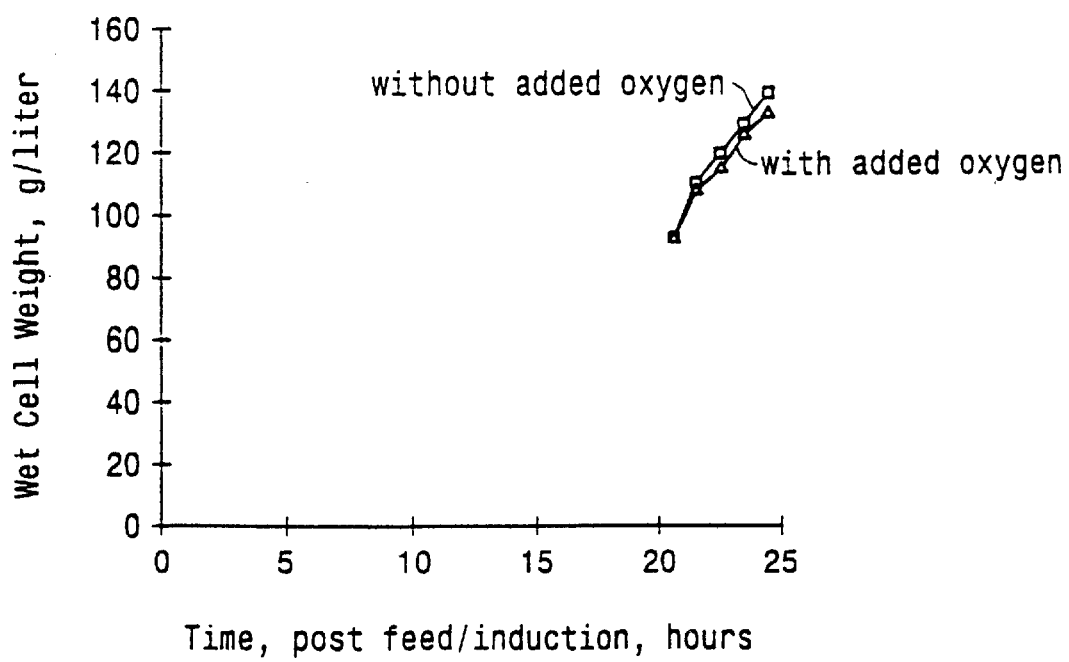

FIGS. 14A and 14B show a comparison of sCTgly production (14A) and cell growth (14B) over time after a typical 1 liter fermentation in the presence of inducer by UGL 165 clone and either in the presence or absence of oxygen supplementation to the air feed. Cell growth was measured as g of wet cell weight per liter of incubation media. sCTgly production was reported as mg of sCTgly excreted per liter of incubation medium. FIGS. 14A and 14B show that added oxygen in the fermentation medium is not critical to cell growth of UGL 165 but is very important in increasing the production of sCTgly.

Figure 15A:
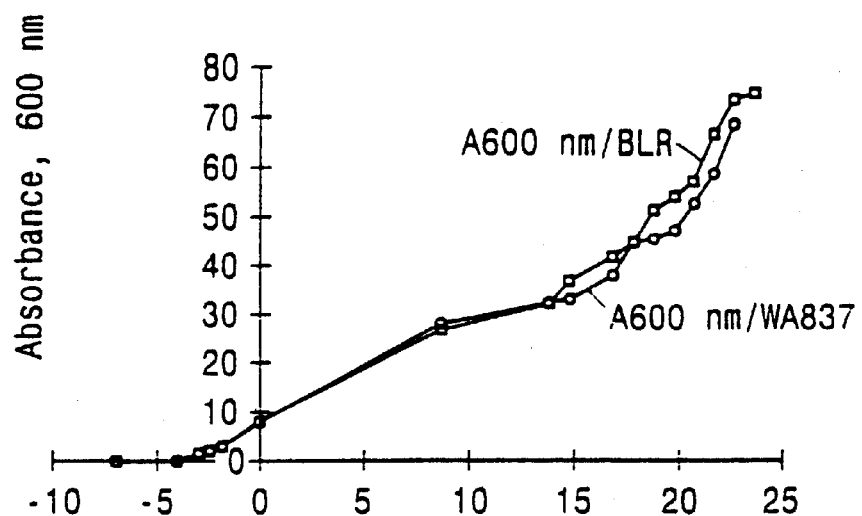
Figure 15B:
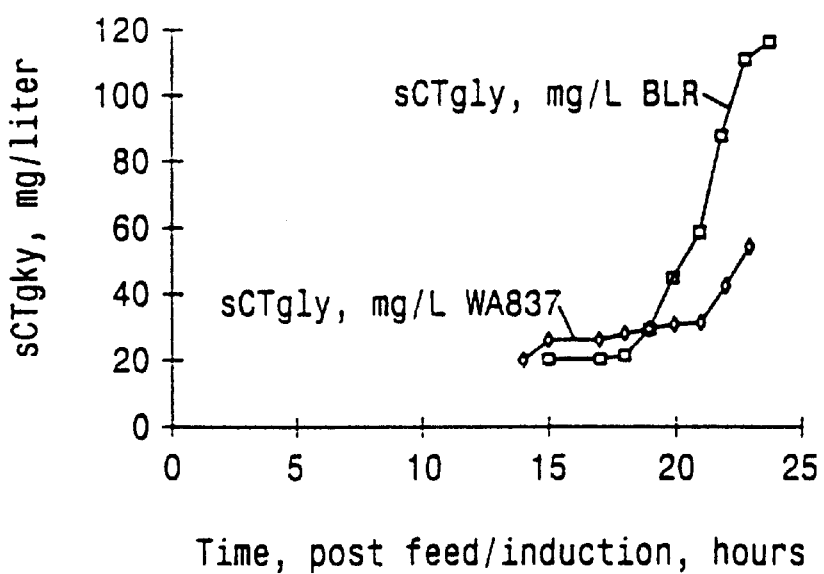

FIGS. 15A and 15B show a comparison of the cell growth (15A) and sCTgly production (15B) over time after a typical 1 liter fermentation in the presence of inducer by the *E. coli* strains WA837 and BLR where each strain is expressing the pSCT-029A vector (UGL164 and UGL165 respectively). Cell growth was measured by light absorbance at a wavelength of 600 nm. sCTgly production was reported as mg of sCTgly excreted per liter of incubation medium. FIGS. 15A and 15B show that the BLR *E. coli* strain is more suited for sCTgly production than the WA837 *E. coli* strain.

Figure 16:
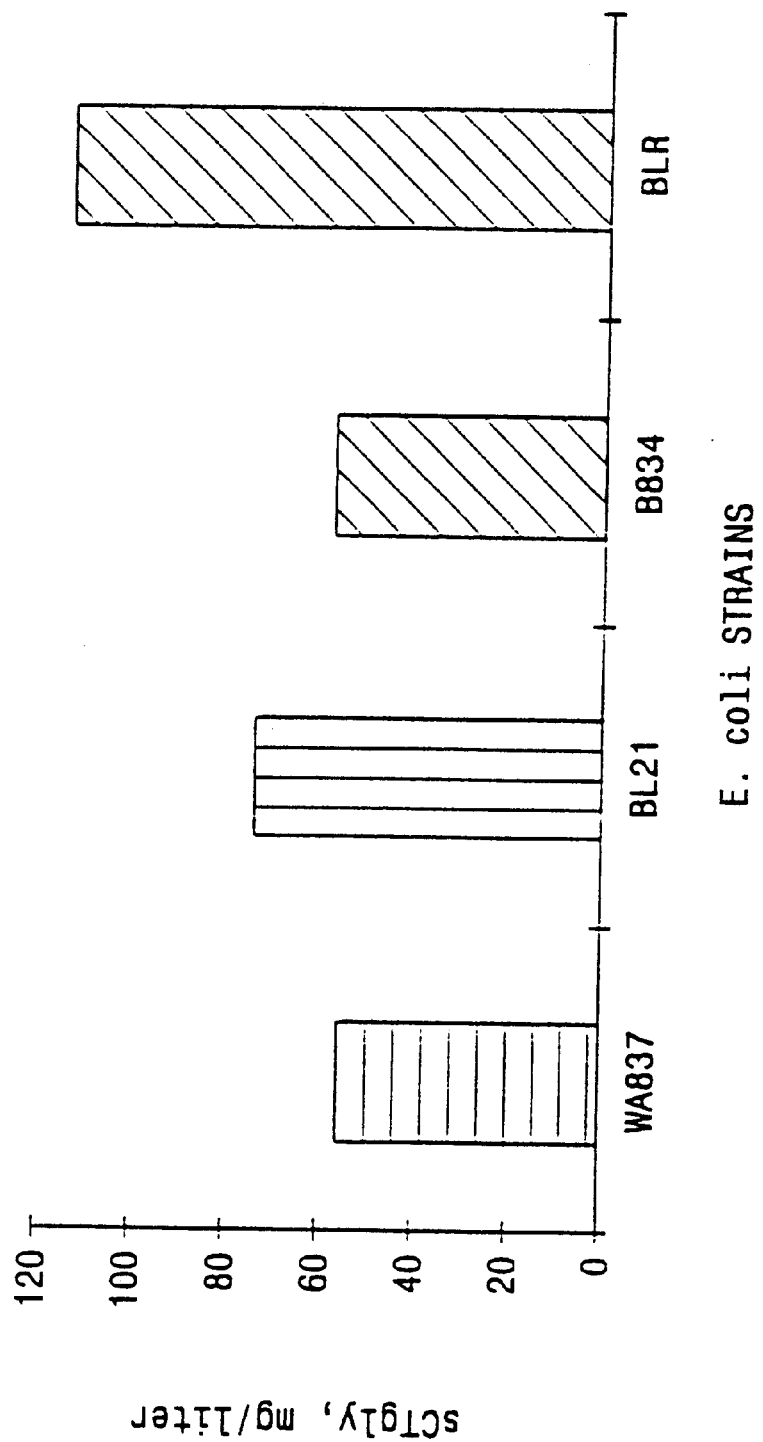

FIG. 16 shows a comparison of sCTgly production after a typical 1 liter fermentation in the presence of inducer by the *E. coli* strains WA837, BLR, BL21 and B834, where each strain is expressing the pSCT-029A vector (UGL164, UGL165, UGL167 and UGL166 respectively). sCTgly production was reported as mg of sCTgly excreted per liter of incubation medium. FIG. 16 shows that the *E. coli* BLR strain is more suited for sCTgly production than each of the WA837, BL21 and B834 *E. coli* strains.

Figure 17:
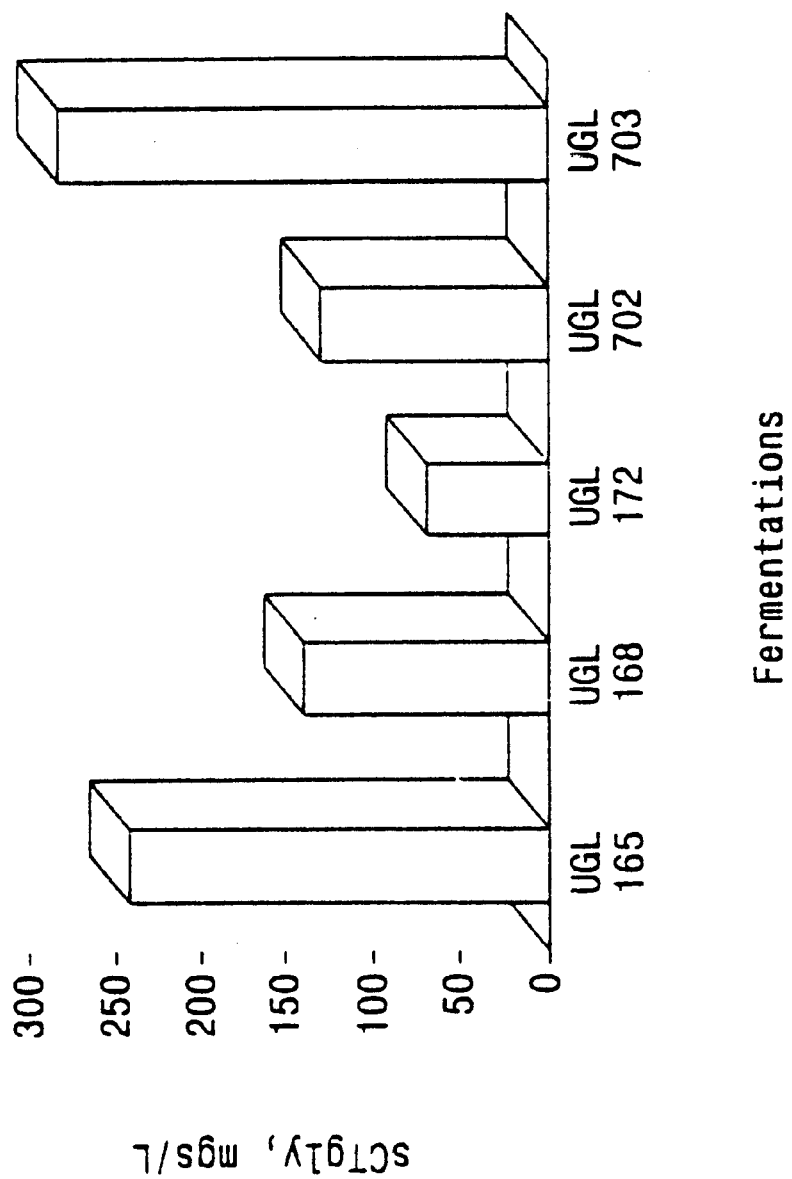

FIG. 17 shows a comparison of the best sCTgly production observed from different experiments after 1 liter fermentations in the presence of inducer by UGL 165 (pSCT-029A in BLR), UGL 168 (pscT-034 in BLR), UGL 172 (pSCT-025 in BLR), UGL 702 (pSCT-037 in BLR) and UGL 703 (pSCT-038 in BLR) clones. sCTgly production was reported as mg of sCTgly excreted per liter of incubation medium. FIG. 17 shows that the digenic UGL 703 and UGL 165 clones are more suited for sCTgly production than the monogenic UGL 172 and UGL 702 clones and the trigenic UGL 168 clone. FIG. 17 also shows that the digenic UGL 703 clone that expresses secretion factors is more suited for sCTgly production than the digenic UGL 165 clone which does not express secretion factors.

DETAILED DESCRIPTION OF THE INVENTION

The present invention permits peptide product yields in excess of 100 mg per liter of media. It does so with novel expression vectors, novel hosts (as transformed, transfected or used in accordance with the invention), novel fermentation processes, or a combination of two or more of the foregoing.

Overview of a Preferred Expression Vector

In one embodiment, the present invention provides an expression vector which comprises a coding region and a control region. The coding region comprises nucleic acids for a peptide product of interest coupled in reading frame downstream from nucleic acids coding for a signal peptide. The control region is linked operably to the coding region and comprises a plurality of promoters and at least one ribosome binding site, wherein at least one of the promoters is selected from the group consisting of tac and lac.

Preferably, the vector comprises a plurality of transcription cassettes placed in tandem, each cassette having the control region and the coding region of the present invention. Such a digenic vector or multigenic vector is believed to provide better expression than would a dicistronic or multicistronic expression vector. This is a surprising improvement over dicistronic or multicistronic expression which is not believed to be suggested by the prior art.

The vector can optionally further comprise nucleic acids coding for a repressor peptide which represses operators associated with one or more of the promoters in the control region, a transcription terminator region, a selectable marker region and/or a region encoding at least one secretion enhancing peptide. Alternatively, in some embodiments, nucleic acids coding for a repressor peptide and a secretion enhancing peptide may be present on a separate vector co-expressed in the same host cell as the vector expressing the peptide product.

Specific examples of constructed expression vectors, and methods for constructing such expression vectors are set forth intra. Many commercially available vectors may be utilized as starting vectors for the preferred vectors of the invention. Some of the preferred regions of the vectors of the invention may already be included in the starting vector such that the number of modifications required to obtain the vector of the invention is relatively modest. Preferred starting vectors include but are not limited to pSP72 and pKK233-2.

It is believed that the novel vectors of the invention impart advantages which are inherent to the vectors, and that those unexpected advantages will be present even if the vectors are utilized in host cells other than the particular hosts identified as particularly useful herein, and regardless of whether the improved fermentation process described herein is utilized.

Likewise, in certain embodiments, particular host cells are identified as being particularly useful in the expression of peptides such as salmon calcitonin precursor and calcitonin gene related peptide precursor. The advantages imparted by specifically utilizing the particular host cells identified herein are believed to exist regardless of whether the expression vector is one of the novel vectors described herein or whether the novel fermentation process described herein is utilized. In other words, it is believed that these host cells will impart significant unexpected advantages even utilizing prior art fermentation or prior art vectors.

The novel fermentation process is believed to provide increased yield because of inherent advantages imparted by the fermentation process. It is believed that these advantages will be present regardless of whether the preferred host cells and/or novel vectors described herein are utilized.

Notwithstanding the foregoing, one preferred embodiment of the invention simultaneously utilizes the improved expression vectors of the invention transformed into the particularly identified host cells of the invention and expressed utilizing the preferred fermentation invention described herein. When all three of these inventions are used in combination, it is believed that a significant enhancement of yield and recovery of product can be achieved relative to the prior art.

The Control Region

The control region is operably linked to the coding region and comprises a plurality of promoters and at least one ribosome binding site, wherein at least one of the promoters is selected from the group consisting of lac and tac. It has surprisingly been found that the foregoing combination of promoters in a single control region significantly increases yield of the peptide product produced by the coding region (as described in more detail intra). It had been expected that two such promoters would largely provide redundant function, and not provide any additive or synergistic effect. Experiments conducted by applicants have surprisingly shown a synergy in using the claimed combination of promoters. Other promoters are known in the art, and may be used in combination with a tac or lac promoter in accordance with the invention. Such promoters include but are not limited to lpp, ara B, trpE, gal K.

Preferably, the control region comprises exactly two promoters. When one of the promoters is tac, it is preferred that the tac promoter be 5' of another promoter in the control region. When one of the promoters is lac, the lac promoter is preferably 3' of another promoter in the control region. In one embodiment, the control region comprises both a tac promoter and a lac promoter, preferably with the lac is promoter being 3' of the tac promoter.

The Coding Region

The coding region comprises nucleic acids coding for a peptide product of interest coupled in reading frame downstream from nucleic acids coding for a signal peptide whereby the coding region encodes a peptide comprising, respectively, from N terminus to C terminus the signal and the peptide product. Without intending to be bound by theory, it is believed that the signal may provide some protection to the peptide product from proteolytic degradation in addition to participating in its secretion to the periplasm.

Many peptide signal sequences are known and may be used in accordance with the invention. These include signal sequences of outer membrane proteins of well-characterized host cells, and any sequences capable of translocating the peptide product to the periplasm and of being post-translationally cleaved by the host as a result of the translocation. Useful signal peptides include but are not limited to Omp A, pel B, Omp C, Omp F, Omp T, β-la, Pho A, Pho S and Staph A.

The peptide product is preferably small enough so that, absent the present invention, it would usually require a fusion partner using prior art technology. Typically, the peptide product has a molecular weight of less than 10 KDa. More preferably, the peptide product has a C-terminal glycine, and is used as a precursor to an enzymatic amidation reaction converting the C-terminal glycine to an amino group, thus resulting in an amidated peptide. Such a conversion is described in more detail infra. Numerous biologically important peptide hormones and neurotransmitters are amidated peptides of this type. For example, the peptide product coded by the coding region may be salmon calcitonin precursor or calcitonin gene related peptide precursor, both of which have C-terminal glycines and both of which may be enzymatically amidated to mature salmon calcitonin or mature calcitonin gene related peptide. Other amidated peptides that may be produced in accordance with the invention include but are not limited to growth hormone releasing factor, vasoactive intestinal peptide and galanin. Other amidated peptides are well known in the art.

Analogs of parathyroid hormone could also be produced in accordance with the invention. For example, a peptide having the first 34 amino acids of parathyroid hormone can provide a function similar to that of parathyroid hormone itself, as may an amidated version of the 34 amino acid analog. The latter may be produced by expressing, in accordance with one or more of the expression systems and methods described herein, the first 34 amino acids of parathyroid hormone, followed by glycine-35. Enzymatic amidation as disclosed herein could then convert the glycine to an amino group.

While preferred embodiments of the direct expression system described herein produce peptides having C-terminal glycine, it is believed that any peptide will enjoy good yield and easy recovery utilizing the vectors, hosts and/or fermentation techniques described herein.

Other Optional Aspects of a Preferred Vector of the Invention or of Other Vectors to be Expressed in the Same Host as the Vector of the Invention Repressor Optionally, the preferred vector of the present invention may contain nucleic acids coding for a repressor peptide capable of repressing expression controlled by at least one of the promoters. Alternatively, however, the nucleic acids coding for a repressor peptide may be present on a separate vector in a host cell with the vector of the present invention. Appropriate repressors are known in the art for a large number of operators. Preferably, the nucleic acids coding for the repressor encode a lac repressor in preferred embodiments of the invention because it represses the lac operator that is included with both tac and lac promoters, at least one of which promoters is always present in preferred vectors of the invention.

Selectable Marker

It is preferred that any of a large number of selectable marker genes (e.g. a gene encoding kanamycin resistance) be present in the vector of the present invention. This will permit appropriate specific selection of host cells that are effectively transformed or transfected with the novel vector of the invention.

Secretion Enhancing Peptide

Nucleic acids coding for at least one secretion enhancing peptide are optionally present in the vector of the present invention. Alternatively, the nucleic acids coding for a secretion enhancing peptide may be present on a separate vector expressed in the same host cell as the vector encoding the peptide product. Preferably, the secretion enhancing peptide is selected from the group consisting of SecY (prlA) or prlA-4. It is pointed out that SecY and prlA are identical, the two terms being used as synonyms in the art. prlA-4 is a known modification of prlA and has a similar function. Another preferred secretion enhancing peptide is SecE also known as "prlG", a term used as a synonym for "SecE". Most preferably, a plurality of secretion enhancing peptides are encoded, at least one of which is SecE and the other of which is selected from the group consisting of SecY (prlA) and prlA-4. The two are believed to interact to aid translocation of the peptide product from cytoplasm to periplasm. Without intending to be bound by theory, these secretion enhancing peptides may help protect the peptide product from cytoplasmic proteases in addition to their secretion enhancing functions.

Host Cell

The present invention also provides a host cell transformed or transfected with any of the vectors of the present invention. Preferably, the host cell is a bacterial cell. More preferably, the host cell is a gram negative bacterial cell. Still more preferably, the host cell is *E. coli*. More preferably, the *E. coli* is strain BLR, BL21 or WA837. Most preferably, the *E. coli* is strain BLR. Also most preferably, the host cell further expresses at least one secretion-enhancing peptide.

The present invention further provides a host cell transformed with an expression vector which comprises a gene for expressing salmon calcitonin precursor or Calcitonin Gene Related Peptide precursor, said host cell being *E. coli* strain BLR. It is believed that BLR expression of these two peptides will be particularly effective even where prior art vectors-are used for the expression. In other words, it is not believed that the novel expression vectors reported herein are required for good expression of these two peptides in a BLR host.

Method of Producing a Heterologous Peptide

Novel fermentation conditions are provided for growing host cells to very high cell densities under culture conditions which permit the diffusion or excretion of the peptide product into the culture medium in high yield.

Host cells useful in the novel fermentation include but are not limited to the host cells discussed supra, and/or host cells transformed or transfected with one or more of the novel expression vectors discussed supra. Other host cells genetically engineered to express peptide product together with a signal region may be used. The cells are placed in a fermenter which preferably includes appropriate means of feeding air or other gases, carbon source, and other components to the media and means for induction of the promoter-Appropriate means for monitoring oxygen content, cell density, pH and the like are also preferred.

Applicants have found that significantly improved yield of peptide product directly expressed into the culture medium is obtained by carefully controlling the average cell growth rate within a critical range between 0.05 and 0.20 doublings per hour. It is preferred that this controlled growth begin in early lag phase of the culture. It is more preferable to maintain average cell growth rate during the fermentation period (i.e. the period during which growth is being controlled as set forth herein), between 0.10 and 0.15 doublings per hour, most preferably 0.13 doublings per hour. Growth rate may be controlled by adjusting any of the parameters set forth infra in the section entitled "Production of sCTgly (Fermentation)", specifically the formula equating the feed rate "Q" to numerous other parameters. Applicants have found that varying the rate of carbon source being fed to the fermenting cells is an advantageous method of maintaining the growth rate within the critical range. In order to maintain the growth rate relatively constant, the amount of carbon source feeding into the fermenter tends to increase proportionally to the growth in number of cells.

Applicants have also discovered that significantly improved yield can be obtained by providing inducer during said fermentation period of controlled growth. Like carbon source, feeding proper amounts of inducer involves increasing the rate of feed proportional to growth in number of cells. Since both carbon source and inducer feed preferably increase in a manner which is linked to cell growth, applicants have found that it is advantageous to mix feed and inducer together and to feed the mixture of the two at the appropriate rate for controlling cell growth (with the carbon source), thus simultaneously maintaining a continuous feed of inducer which stays at a constant ratio relative to the amount of carbon source. However, it is of course possible to feed carbon source and inducer separately. Even then, however, if a chemical inducer that may be toxic to the cells in large amounts is used, it is desirable that the inducer and carbon source be added during each hour of culturing in amounts such that the weight ratio of the inducer added in any given hour to the carbon source added in that same hour does not vary by more than 50% from the ratio of the amount of inducer added during the entirety of the fermentation process (controlled growth period) to amount of carbon source added during the entirety of the fermentation process. The 50% variance is measured from the lower ratio of two ratios being compared. For example, where the ratio of carbon source to inducer for the entire fermentation is 2 to 1, the ratio in any given hour is preferably no higher than 3 to 1 and no lower than 1.333 to 1. It is also possible to induce one or more of the promoters during growth by other means such as a shift in temperature of the culture or changing the concentration of a particular compound or nutrient.

When external carbon source feed is used as the method of controlling cell growth, it is useful to wait until any carbon sources initially in the media (prior to external carbon feed) have been depleted to the point where cell growth can no longer be supported without initiating external carbon feed. This assures that the external feed has more direct control over cell growth without significant interference from initial (non-feed) carbon sources. An oxygen source is preferably fed continuously into the fermentation media with dissolved oxygen levels being measured. An upward spike in the oxygen level indicates a significant drop in cell growth which can in turn indicate depletion of the initial carbon source and signify that it is time to start the external feed.

It has been unexpectedly found that peptide product yield increases as oxygen saturation of the fermentation media increases. This is true even though lower oxygen saturation levels are sufficient to maintain cell growth. Thus, during the entire fermentation process, it is preferred that an oxygen or oxygen enriched source be fed to the fermentation media, and that at least 20% and preferably at least 50% oxygen saturation be achieved. As used herein, "oxygen saturation" means the percentage of oxygen in the fermentation medium when the medium is completely saturated with ordinary air. In other words, fermentation media saturated with air has an "oxygen saturation" of 100%. While it is difficult to maintain oxygen saturation of the fermentation medium significantly above 100%, i.e. above the oxygen content of air, this is possible, and even desirable in view of higher oxygen content providing higher yields. This may be achieved by sparging the media with gases having higher oxygen content than air.

Significant yield improvement may be achieved by maintaining oxygen saturation in the fermentation medium at no lower than 70%, especially no lower than 80%. Those levels are relatively easy to maintain.

Faster agitation can help increase oxygen saturation. Once the fermentation medium begins to thicken, it becomes more difficult to maintain oxygen saturation, and it is recommended to feed gases with higher oxygen content than air at least at this stage. Applicants have found that ordinary air can be sufficient to maintain good oxygen saturation until relatively late in the fermentation period. Applicants have supplemented the air feed with a 50% oxygen feed or a 100% oxygen feed later in the fermentation period. Preferably, the host cell is cultured for a period between 20 and 32 hours (after beginning controlled growth), more preferably between 22 and 29 hours, most preferably for about 24–27 hours.

Preferably, the host cells are incubated at a temperature between 20 and 35° C., more preferably between 28 and 32° C., more preferably between 29.5 and 30.5° C. A temperature of 30° C. has been found optimal in several fermentations conducted by applicants.

Preferably, the pH of the culturing medium is between 6.0 and 7.5, more preferably between 6.6 and 7.0, with 6.78–6.83 (e.g. 6.8) being especially preferred.

In preferred embodiments, fermentation is carried out using hosts transformed with an expression vector having a control region that includes both a tac and a lac promoter and a coding region including nucleotides coding for a signal peptide upstream of nucleotides coding for salmon calcitonin precursor. Such an expression vector preferably includes a plurality, especially two, transcription cassettes in tandem. As used herein, the term "transcription cassettes in tandem" means that a control and coding region are followed by at least one additional control region and at least one additional coding region encoding the same peptide product as the first coding region. This is to be distinguished from the dicistronic expression in which a single control region controls expression of two copies of the coding region. The definition will permit changes in the coding region that do not relate to the peptide product, for example, insertion, in the second transcription cassette, of nucleotides coding a different signal peptide than is coded in the first transcription cassette.

Numerous carbon sources are known in the art. Glycerol has been found effective. Preferred methods of induction include the addition of chemical inducers such as IPTG and/or lactose. Other methods such as temperature shift or alterations in levels of nutrient may be used. Other induction techniques appropriate to the operator or the promoter in the control region (or one of the plurality of promoters being used where more than one appears in the control region) may also be used.

It is typical that production of peptide product drops significantly at about the same time that growth of the cells in the fermentation media becomes unsustainable within the preferred growth rate discussed supra. At that point, fermentation is stopped, carbon source and inducer feed and oxygen flow are discontinued. Preferably, the culture is quickly cooled to suppress activity of proteases and thus reduce degradation of the peptide product. It is also desirable to modify pH to a level which substantially reduces proteolytic activity. When salmon calcitonin precursor is produced using preferred vectors and host cells of the invention, proteolytic activity decreases as pH is lowered. This acidification preferably proceeds simultaneously with cooling of the media.[1] The preferred pH ranges are discussed in more detail infra. The same assay as is being used for measuring fermentation product can be used to measure degradation at different pH levels, thus establishing the pH optimum for a given peptide and its impurities.

[1] or may be carried out after removal of the bacterial cells

Recovery of the Heterologous Peptide

The present invention further provides a method for recovering the peptide product which comprises separating the host cells from the culture medium and thereafter subjecting the culturing medium to at least one type of chromatography selected from the group consisting of gel filtration, ion-exchange (preferably cation exchange when the peptide is calcitonin), reverse-phase, affinity and hydrophobic interaction chromatography. In a peptide containing cysteine residues, S-sulfonation may be carried out prior to or during the purification steps in order to prevent aggregation of the peptide and thereby increase the yield of monomeric peptide. Preferably, three chromatography steps are used in the following order: ion exchange chromatography, reverse-phase chromatography and another ion exchange chromatography.

After fermentation is completed, the pH of the culture medium is optionally altered to reduce the proteolytic activity. The assay used to measure product production can also be used to measure product degradation and to determine the best pH for stability. Where salmon calcitonin precursor is produced in accordance with the invention, a pH between 2.5 and 4.0 is preferred, especially between 3.0 and 3.5. These pH ranges also are believed to aid retention of salmon calcitonin precursor on cation exchange columns, thus providing better purification during a preferred purification technique described herein.

Also optionally, the temperature of the medium, after fermentation is completed, is lowered to a temperature below 1° C., preferably between 3° C. to 5° C., most preferably 4° C. This is also believed to reduce undesirable protease activity.

The present invention fur-.her provides a method of producing an amidated peptide product comprising the steps of: culturing, in a culture medium, any of the host cells of the present invention which express a peptide product having a C-terminal glycine; recovering said peptide product from said culture medium; amidating said peptide product by contacting said peptide product with oxygen and a reducing agent in the presence of peptidyl glycine α-amidating monooxygenase, or peptidyl glycine α-hydroxylating monooxygenase. If peptidyl glycine α-amidating monooxygenase is not used hereinabove, and if the reaction mixture is not already basic, then increasing pH of the reaction mixture until it is basic. Amidated peptide may thereafter be recovered from the reaction mixture preferably utilizing the purification technique described infra in Example 6.

Preferably, the host cell is cultured in a culture medium in the presence of an inducer, while maintaining an average cell growth rate during culturing between 0.05 and 0.20 doublings per hour.

Experimental Details pSCT-037 and pSCT-038 Cloning Strategy

The construction of pSCT-038 and pSCT-037 is comprised of eight parts converging to create the intermediate vectors needed to construct the final desired expression plasmids. All genes and fragments that were used or constructed outside of the text description for this project are listed in Table 1.

Part I Construction of pSCT-018D

Figures 1, 1A:
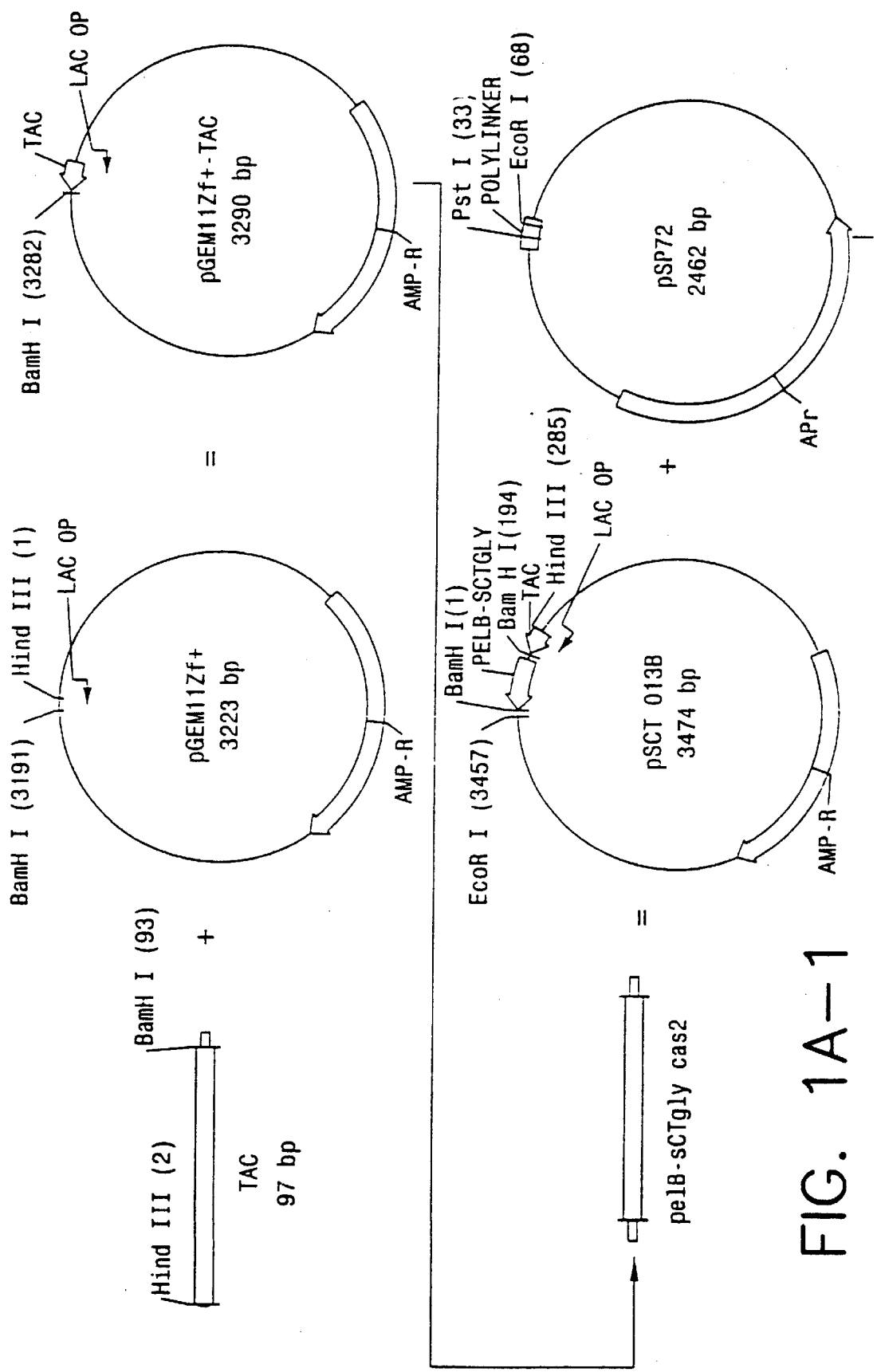
FIGS. 1A and 1B show a schematic diagram of the construction of the pSCT-016B vector (1A) which is used in the construction of the pSCT-018D vector (1B) which is in turn used in the construction of vector pSCT-025.
Figures 1, 1A, 2:
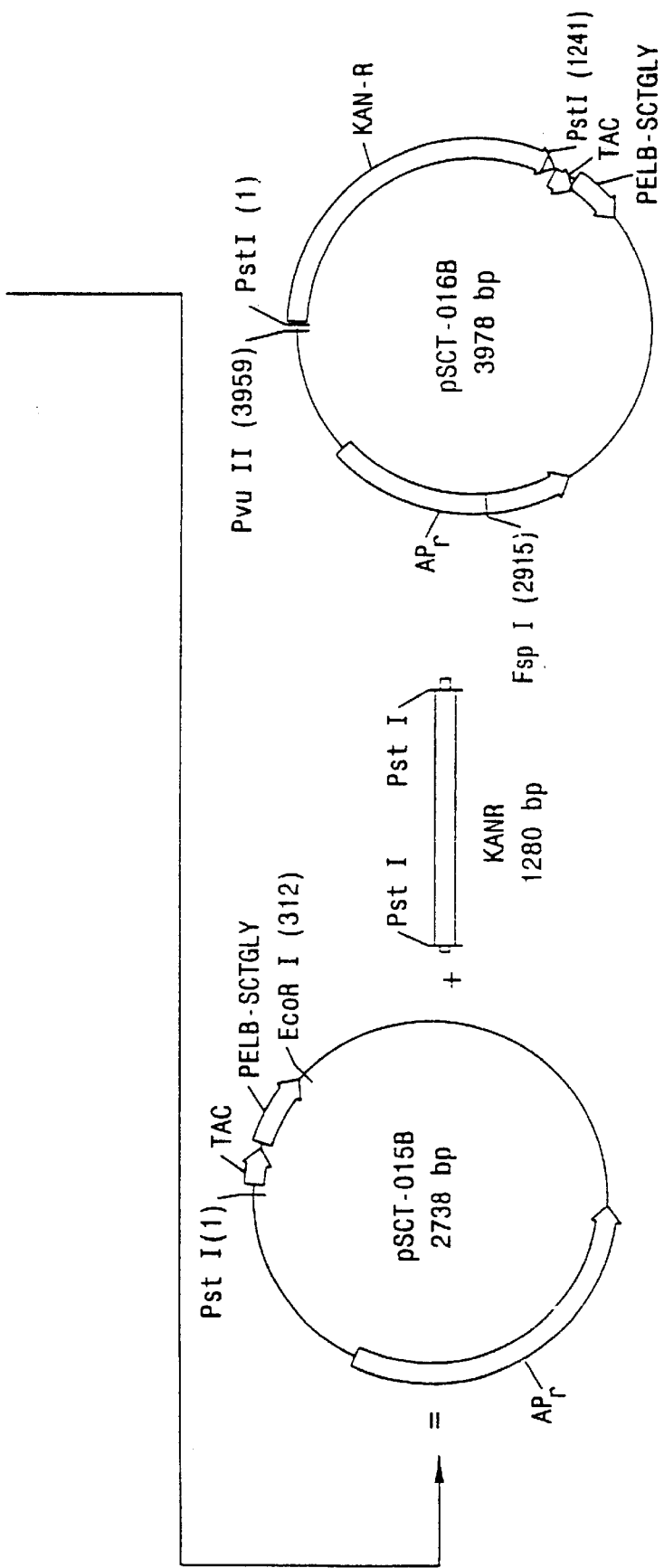
FIG. 2 shows a schematic diagram of the construction of the pSCT-019 vector. The LAC-OMPASCTGLY cassette used in the construction of pSCT-025 was made by polymerase chain reaction (PCR) amplification of a portion of pSCT-019.
Figures 1, 1B:
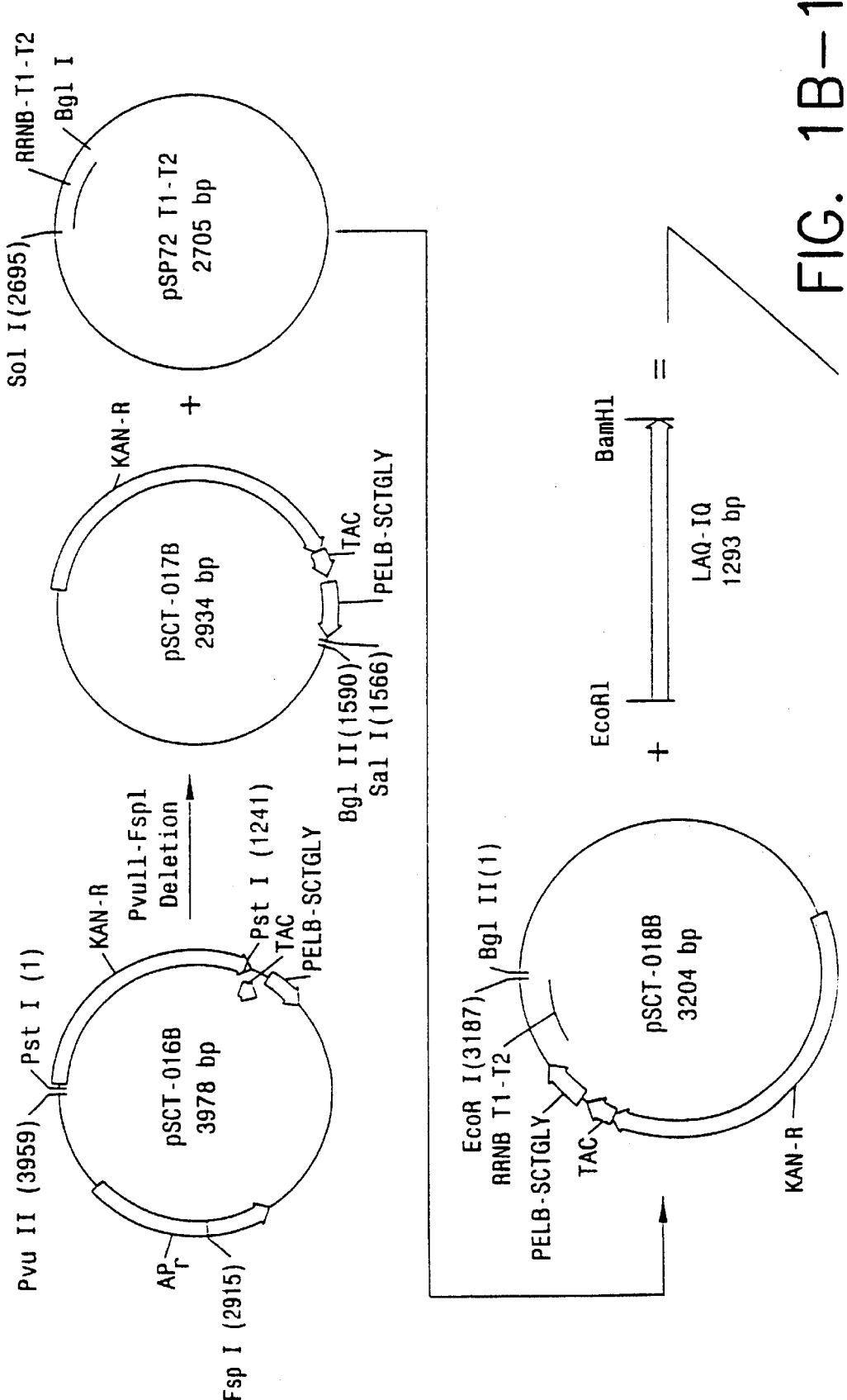
Figures 1, 1B, 2:
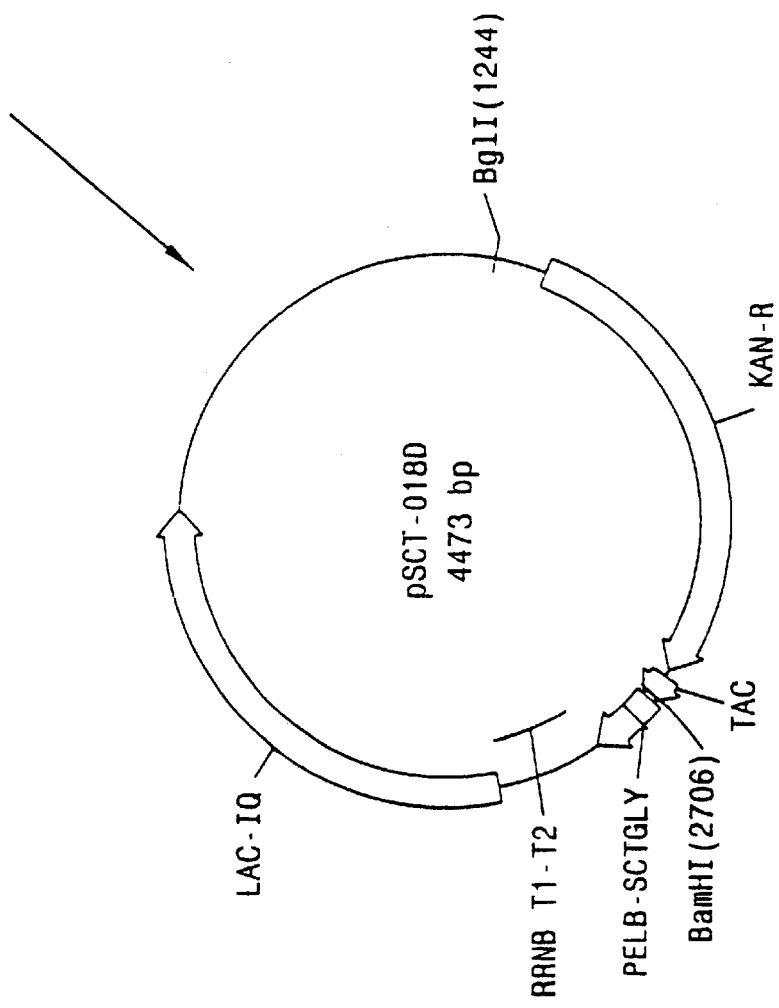
Figure 2A:
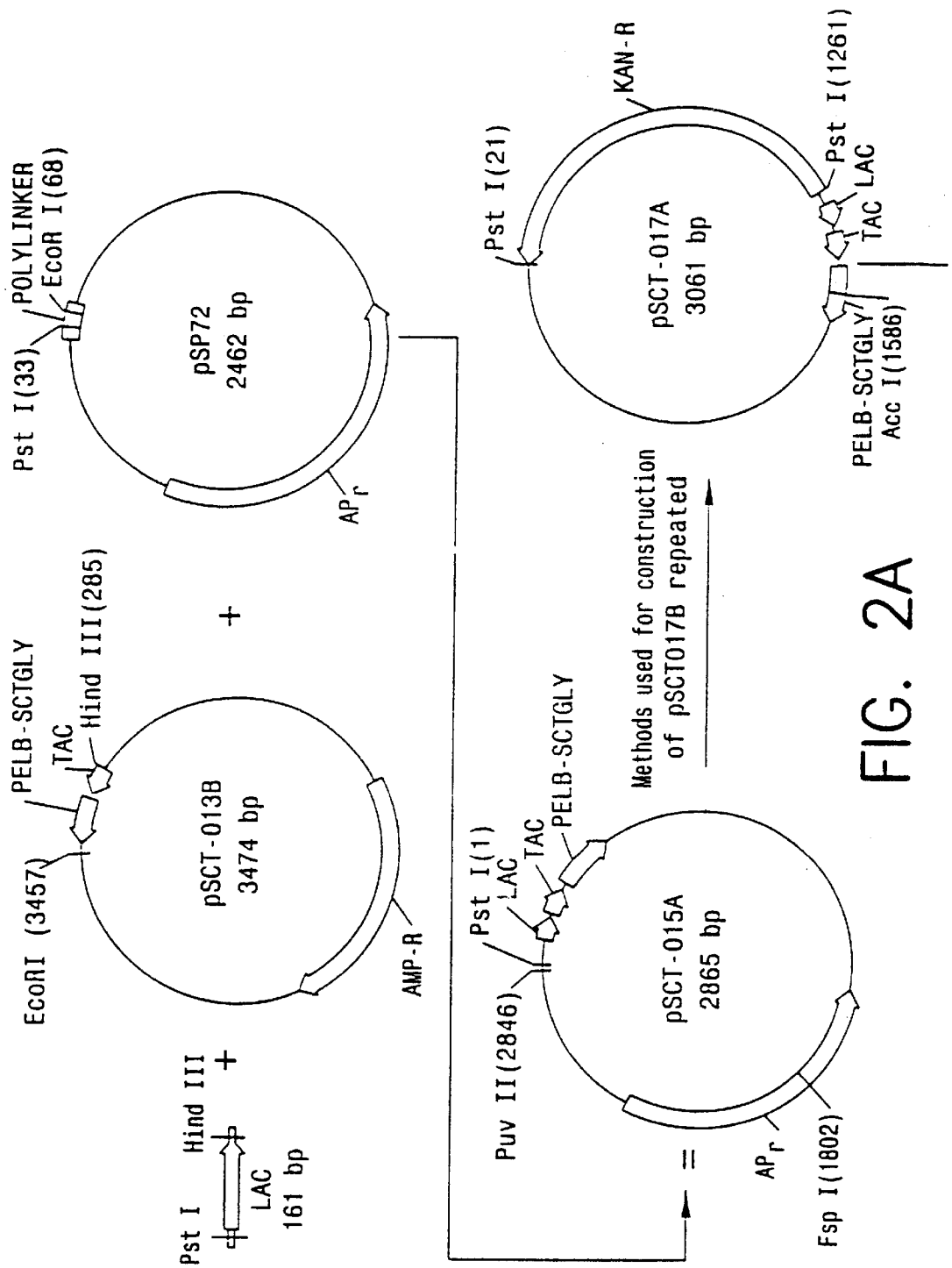
Figures 2, 2A, 2B:
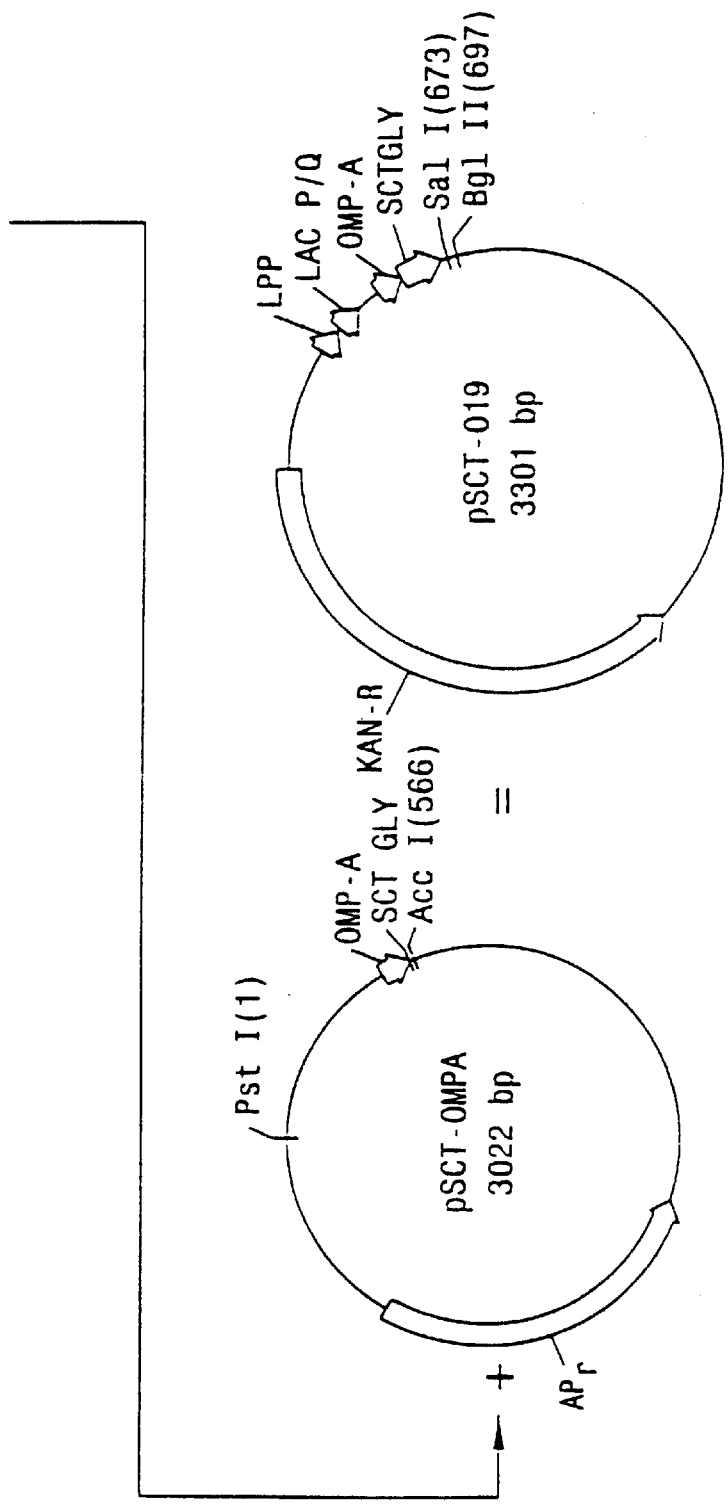

The TAC promoter cartridge (Table 1) was subcloned into pGEM11ZF+ (Table 1) as a Hind III-Bam HI fragment creating pGEM11ZF+TAC. The pelB-sCTgly cas2 gene (Table 1) was ligated downstream of the tac promoter (in pGEM11ZF+TAC) into the Bam HI site to create the expression vector pSCT-013B. The tac-pelBsCTgly operon was cut from pSCT-013B using Hind III and Eco RI. This fragment was then ligated, along with a Hind III-Pst I adapter, into pSP72 (Table 1) creating pSCT-015B. The kanamycin resistance gene was then ligated into the Pst I site of pSCT-015B, creating pSCT-016B. The 5' coding and control region of the 3-lactamase gene (ampicillin resistance) was deleted by cutting the vector with Pvu II and Fsp I followed by religation creating pSCT-017B. The Tl-T2 transcription terminator from pSP72 T1–T2 (Table 1) was then cut and ligated into PSCT-017B using Sal I and Bgl II sites creating pSCT-018B. The LAC-IQ gene (Table 1) containing Bam HI and Eco RI sites was then ligated into the Bgl II—Eco RI sites of PSCT-018B creating pSCT-018D (see FIGS. 1A and 1B)

Part II Construction of pSCT-019

The lac P/O (Table 1) with sites Pst I and Hind III and a Hind III-Eco RI fragment from pSCT-013B (containing tac-pelBsCTgly) were inserted, in a three way ligation, into the Pst I and Eco RI sites of pSP72 creating pSCT-015A. As described in the construction of pSCT-017B, the Kan-R gene was inserted and the β-lactamase gene was removed from pSCT-015A to create pSCT-016A and pSCT-017A. The lpp-lac-ompAsCTgly (Table I) Pst I—Acc I fragment (17 base pairs of the 5' coding sequence of sCTgly are also present) was cut from pSP72-OMPA and ligated into the compatible sites in pSCT-017A to create pSCT-019 (see FIG. 2).

Part III Construction of pSCT-025

Figure 3A:
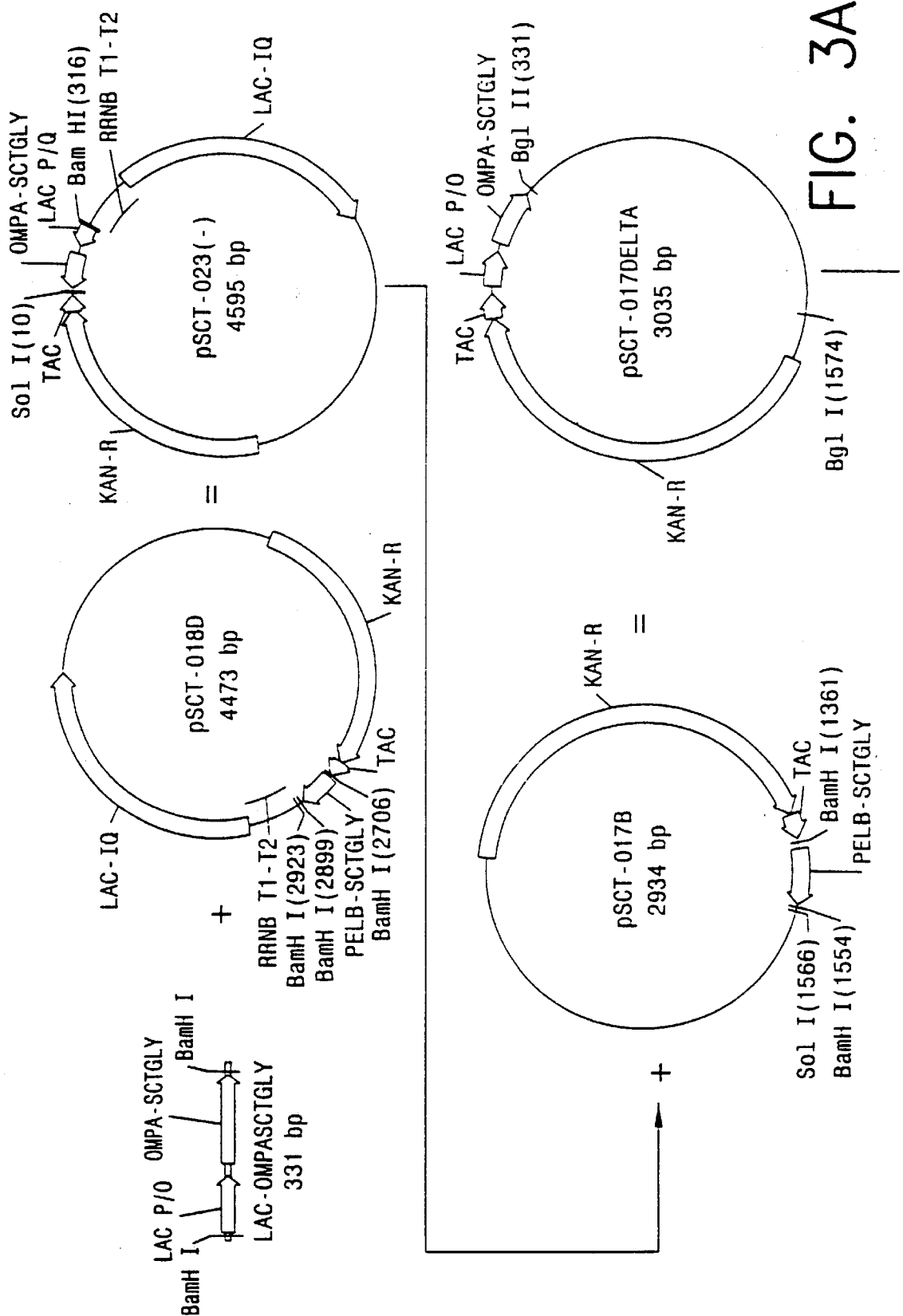
FIG. 3 shows a schematic diagram of the construction of the pSCT-025 vector which was used in the construction of vectors pScT-029A, pSCT-025A, pSCT-037 and pSCT-038.
Figures 3, 3A, 3B:
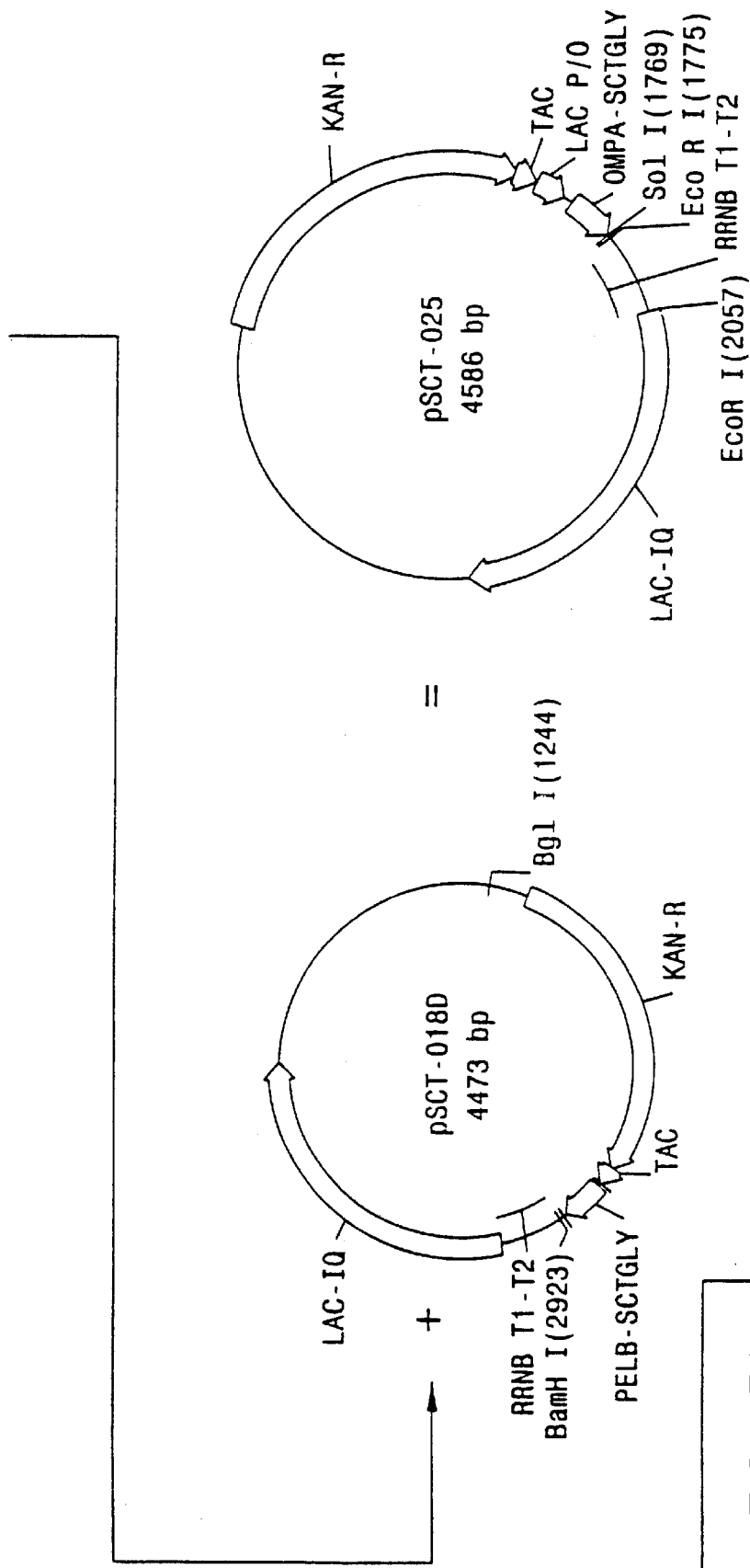

A Bam HI fragment of the PCR amplified operon lac-ompAsCTgly (Table 1) was ligated into the Bam HI site of pSCT-018D, replacing the pelBsCTgly gene creating pSCT-023(-). The (-) signifies that the insert was inserted in the reverse orientation in relation to the tac promoter. The lac-ompAsCTgly operon was then cut from pSCT-023(-), using Bam HI and Sal I, then ligated into the compatible sites of pSCT-017B creating pSCT-017 DELTA. The larger Bgl I-Bgl II fragment containing the kanamycin resistance gene, tac-lac promoters and ompAsCTgly was cut from pSCT-017 DELTA and ligated into the Bgl I-Bam HI sites of pSCT-018D creating pSCT-025 (see FIG. 3).

Part IV Construction of pSCT-029A

Figure 4A:
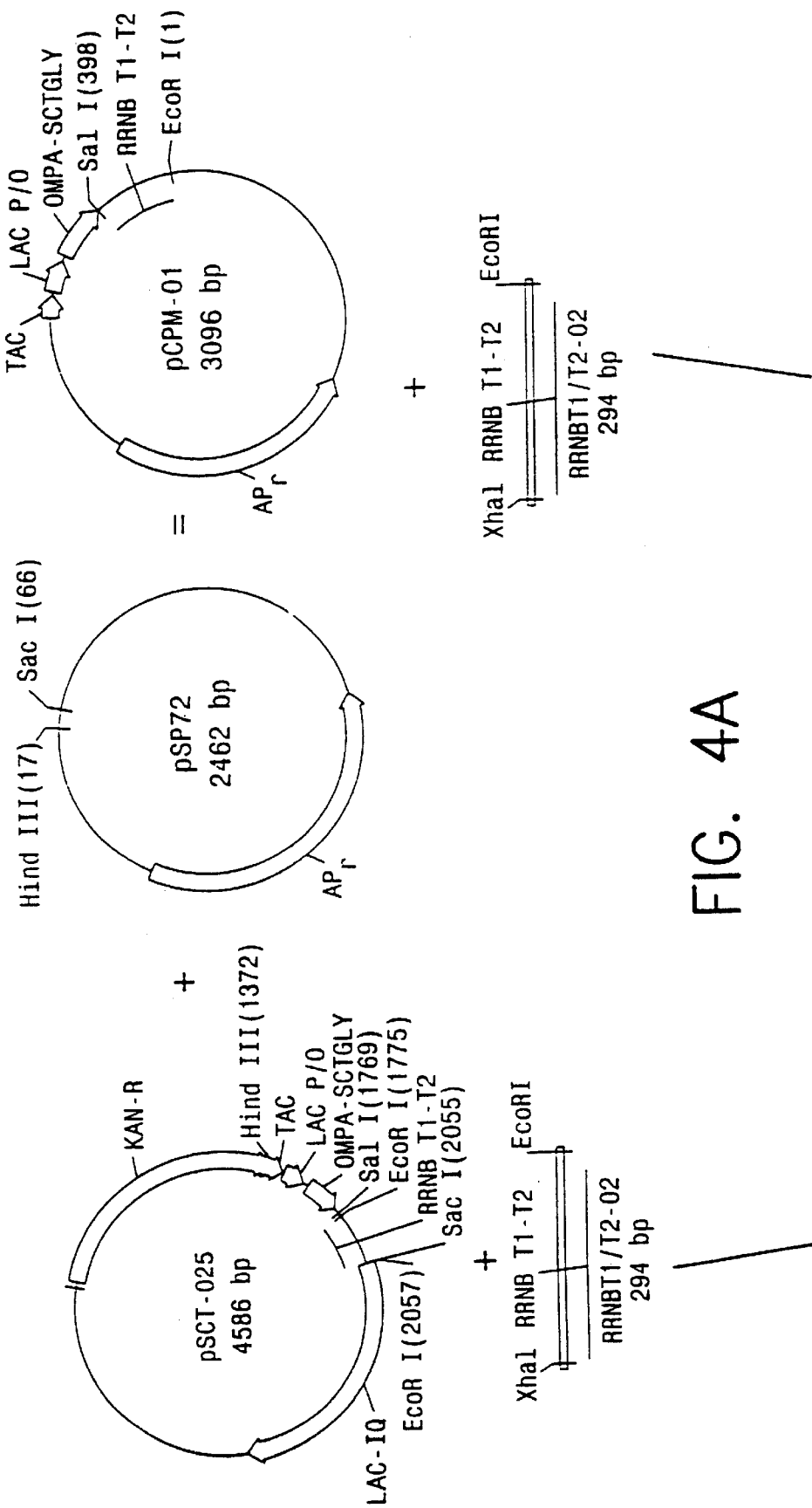
FIG. 4 shows a schematic diagram of the construction of the pSCT-029A vector which was used in the construction of vector pSCT-038 and pSCT-034. In addition, pSCT-029A was used to transform E. coli BLR and produce the novel digenic UGL 165 clone.

A PCR product of RRNB T1–T2–02 (Table 1), containing Xho I and Eco RI sites, was ligated into the Sal I—Eco RI sites of pSCT-025 creating pSCT-025A. A Hind III-Sac I fragment cut from pSCT-025, containing the tac-lac-ompAsCTgly RRNB T1–T2 terminators gene cartridge, was ligated into the compatible sites of pSP72 creating pCPM-01. The pCPM-01A vector was constructed using the same method described for pSCT-025A. The pSCT-025A and pCPM-01A plasmids differ from the pSCT-025 and pSCT-01 plasmids in the types of restriction sites present upstream and downstream of the RRNB T1–T2 transcription terminator. An Xho I-Eco RI fragment, containing the tac-lac-ompAsCTgly RRNB T1–T2 terminators gene cartridge was cut from pCPM-01A and ligated into the Sal I-Eco RI sites of pSCT-025A creating the digenic expression vector pSCT-029A (FIG. 4). The methods used to create pSCT-029A can be repeated to create additional polygenic expression vectors, as shown below for the construction of pSCT034.

Part V Construction of pSEC-B

Figure 5A:
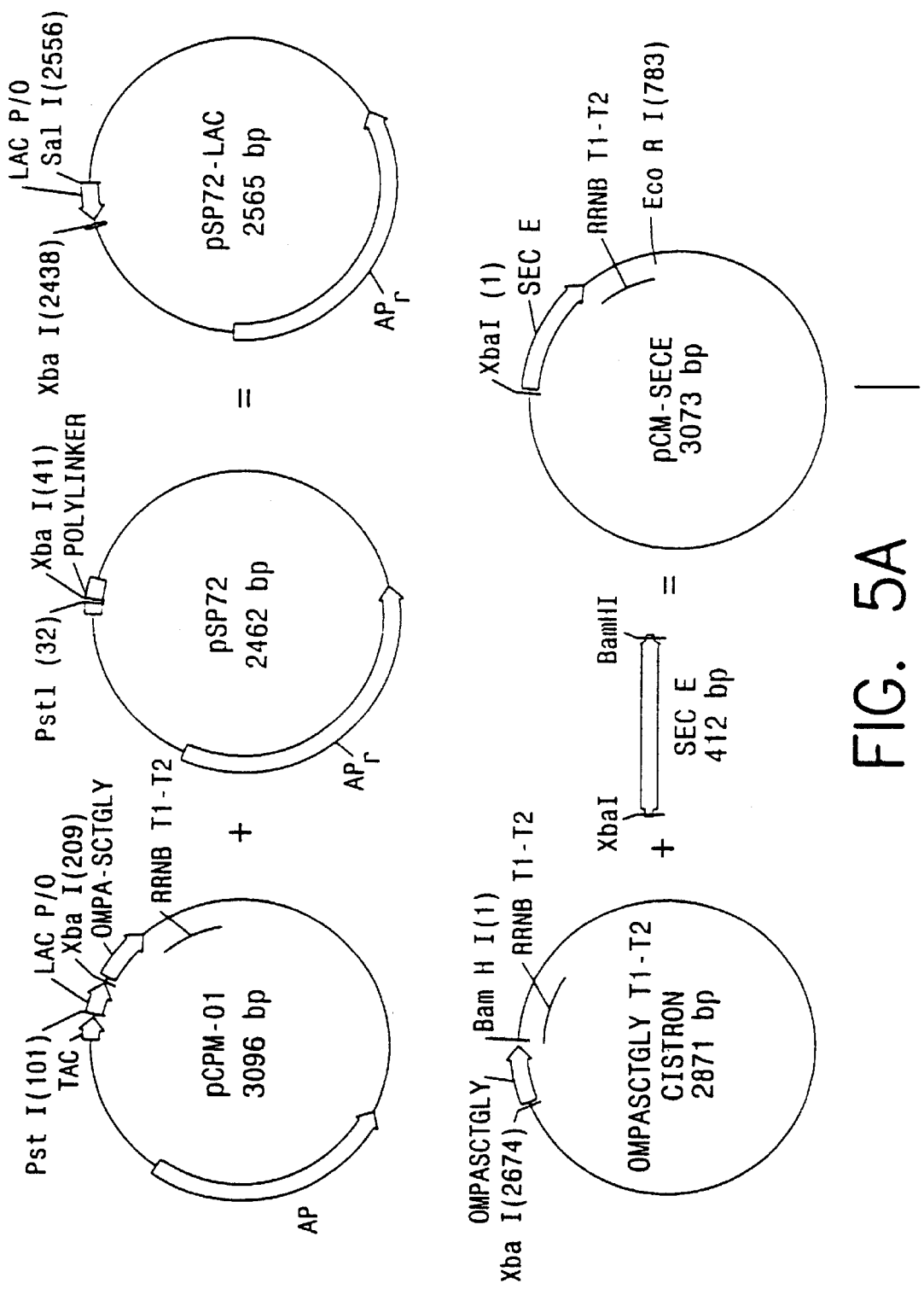
FIG. 5 shows a schematic diagram of the construction of the pSEC-E vector which was used in the construction of vector pSEC-EY.
Figures 5, 5A, 5B:
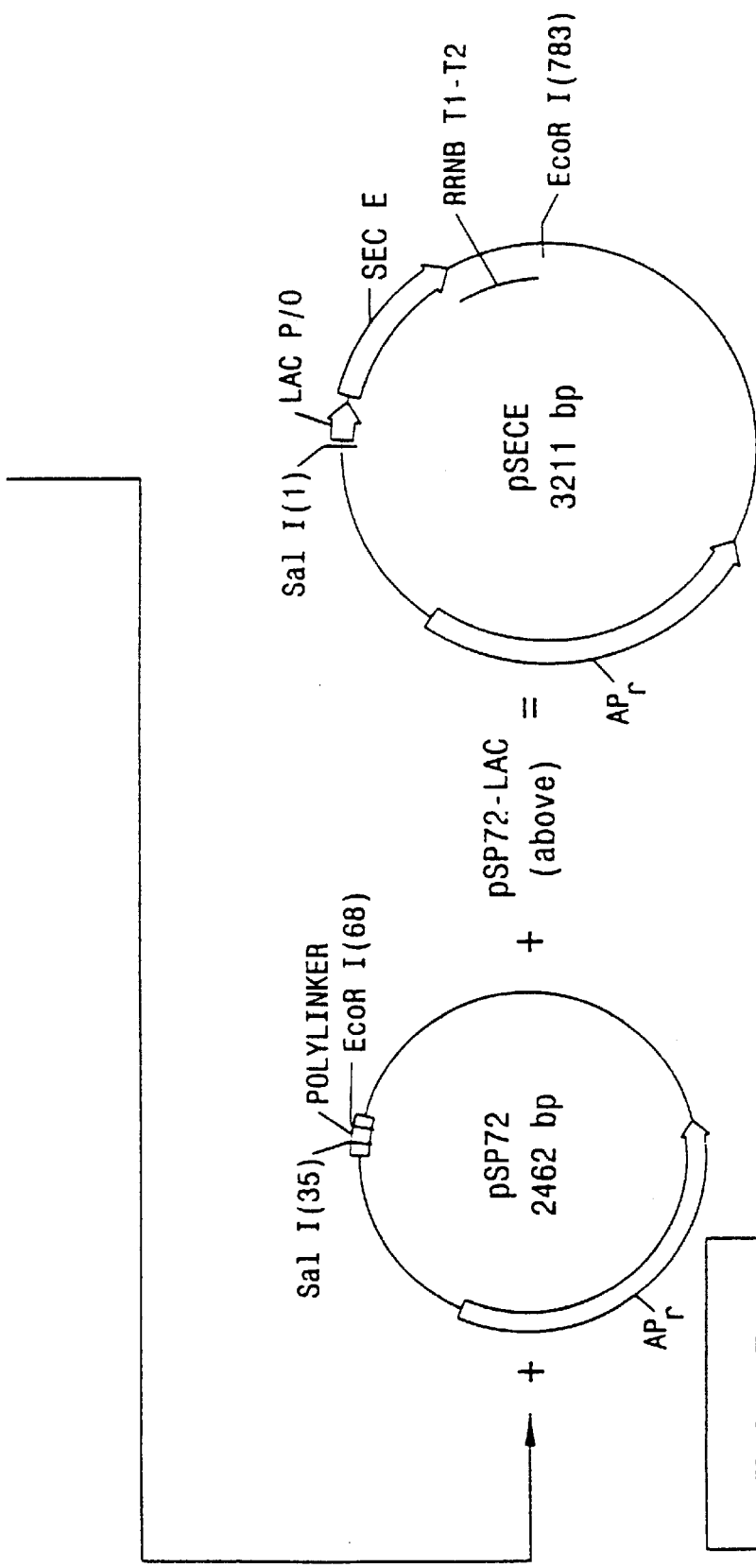

The vector pCPM-01 was digested with Pst I and Xba I to excise the lac P/O, which was then ligated into the compatible sites of pSP72. The PCR amplified secE gene (Table I) containing Xba I and Bam HI cloning sites was ligated into the compatible sites of the ompAsCTgly T1–T2 cistron cloning vector (Table 1) creating pCM-SECE. The secE and T1–T2 terminators were cut from pCM-SECE as an Xba I-Eco RI fragment and ligated along with an Xba I-Sal I fragment, containing the lac P/O (cut from pSP72-lac), into the Sal I-Eco RI sites of pSP72 creating pSEC-E (see FIG. 5)

Part VI Construction of pPRLA-4 (prlA-4 is a Mutant Allele of the prIA or secY Gene)

Figure 6A:
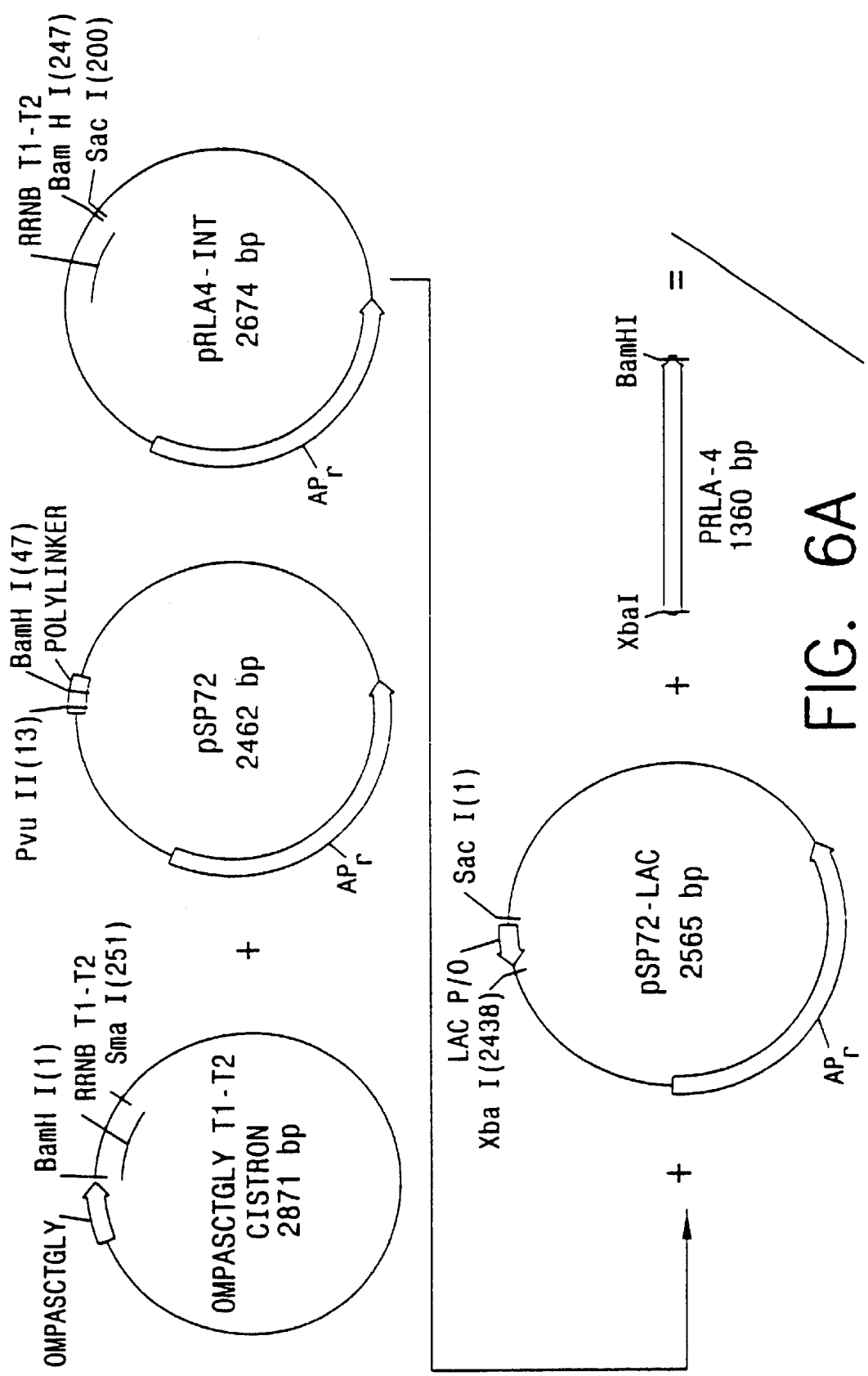
FIG. 6 shows a schematic diagram of the construction of the pPRLA4 vector which was used in the construction of vector pSEC-EY.
Figures 6, 6B:
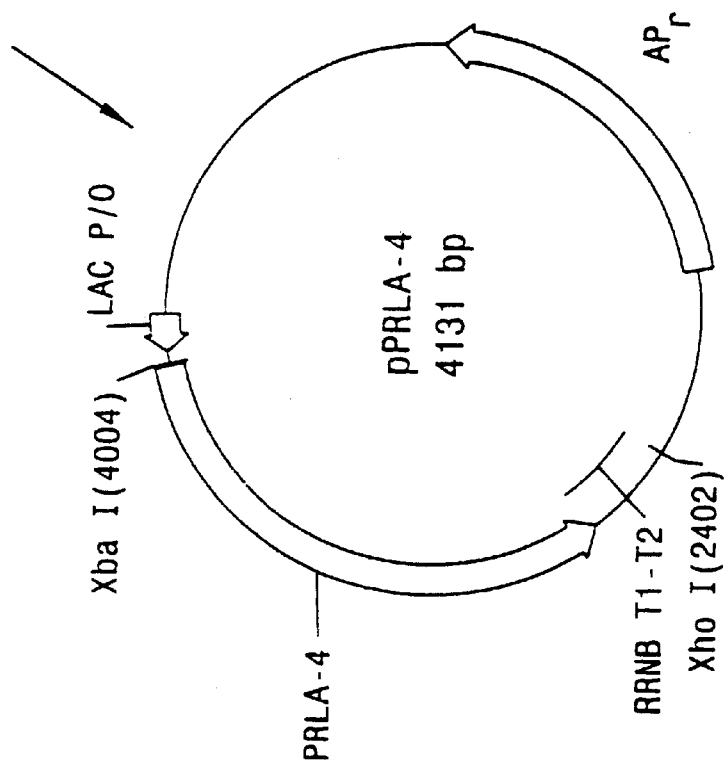

The T1–T2 terminator region of the ompAsCTgly T1–T2 cistron vector was excised using Bam HI and Sma I, which was then ligated into the Pvu II and Bam HI sites of pSP72 creating the PRLA4-INT intermediate cloning vector. The lac P/O was cut from pSP72-LAC with Xba I and Sac I and ligated along with the prlA-4 PCR fragment (Table I), containing Xba I and Bam HI restriction sites, into the Sac I—Bam HI sites of PRLA4-INT creating pPRLA-4 (see FIG. 6).

Part VII Construction of pSEC-EY

Figure 7A:
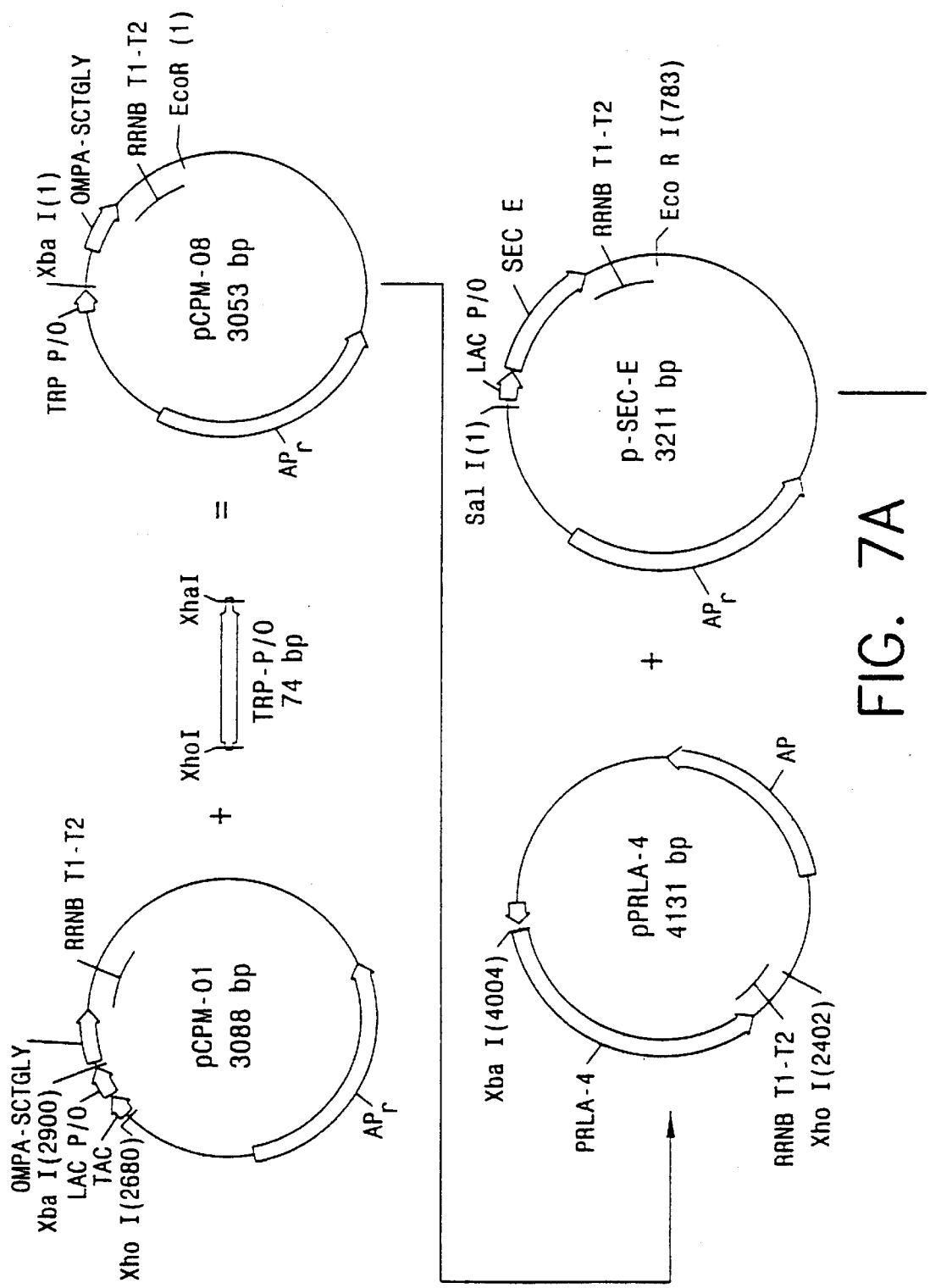
FIG. 7 shows a schematic diagram of the construction of the pSEC-EY vector which was used in the construction of vector pSCT-037 and pSCT-038.
Figures 7, 7A, 7B:
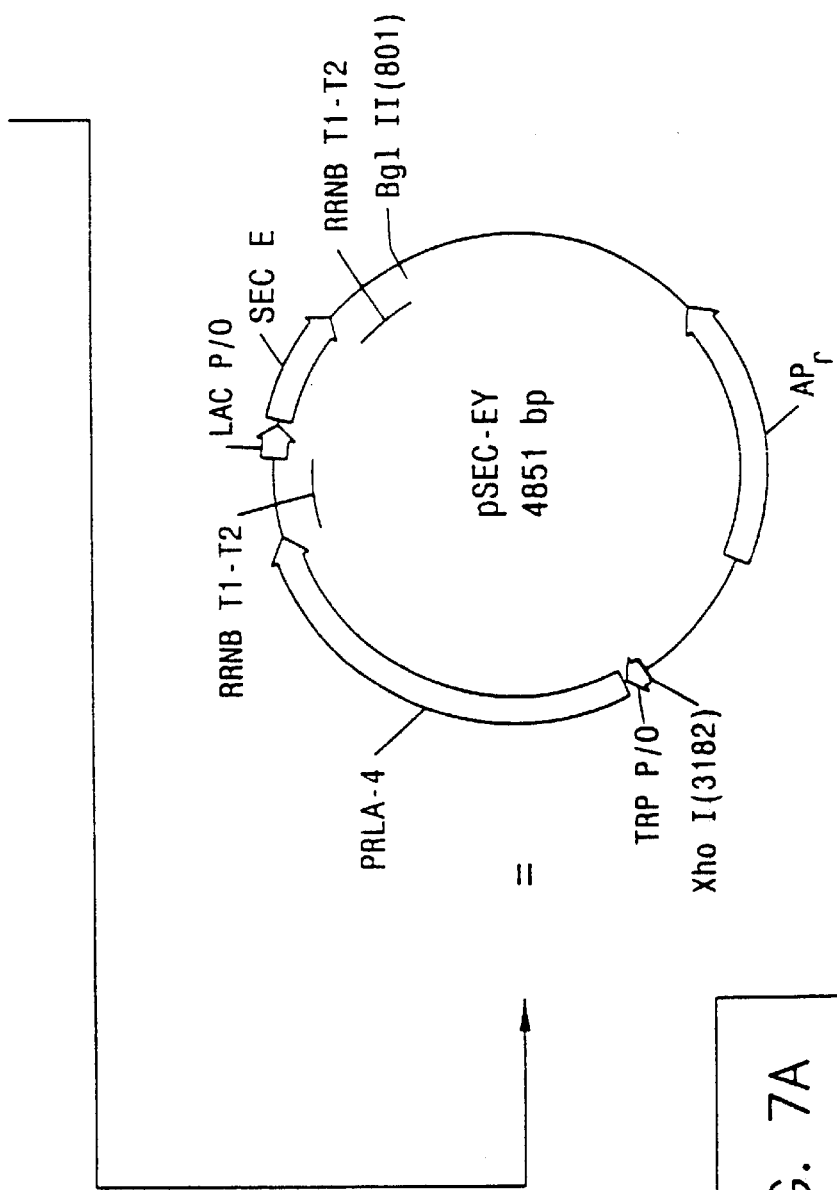

A synthetic oligonucleotide fragment containing the trpE P/O sequence (Table I) was subcloned into the Xho I-Xba I sites of pCPM-01A creating pCPM-08. The prlA-4 and T1–T2 sequences were cut from pPRLA-4 with Xba I and Xho I and ligated with a Sal I-Eco RI fragment from pSEC-E, containing the lac-secE-T1–T2 operon, into the Xba I and Eco RI sites of pCPM-08 creating pSEC-EY (see FIG. 7).

Part VIII Construction of pSCT-037 and pSCT-038

Figure 8A:
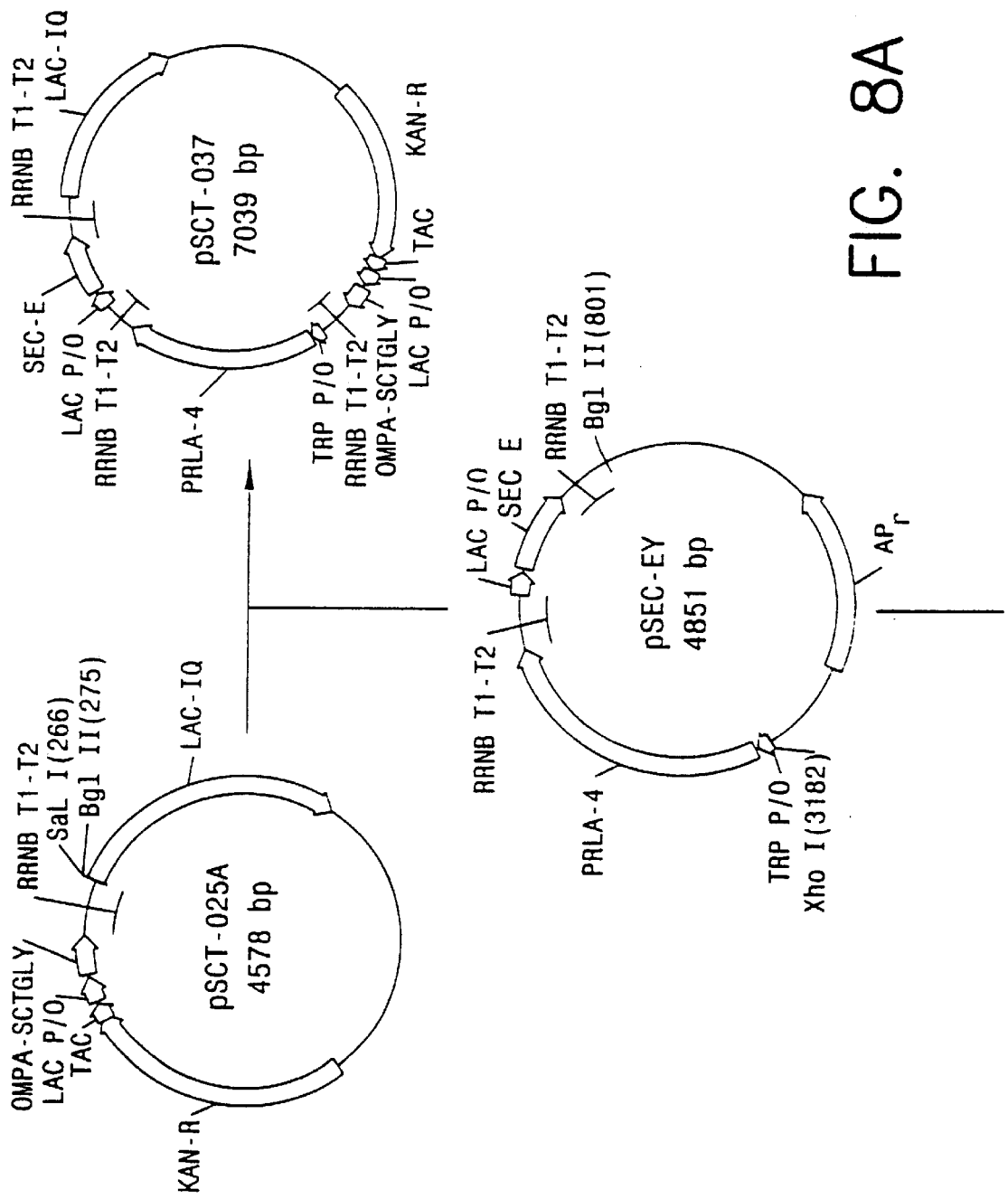
FIG. 8 shows a schematic diagram of the construction of pSCT-037 and pSCT-038 vectors pSCT-037 was used to transform *E. coli* BLR and produce the monogenic UGL 702 clone pSCT-038 was used to transform *E. coli* BLR and produce the digenic UGL 703 clone. pSCT-038 contains two copies of the ompA-sCTgly operon (encoding the OmpA signal together with salmon calcitonin precursor) making it a novel digenic expression vector. It also contains copies of genes encoding two sec machinery proteins which enhance translocation across the inner membrane into the periplasmic space. The following is a list of abbreviations used in describing this vector of FIG. 8.

The secE and prlA-4 coding region were cut from pSEC-EY with Xho I and Bgl II. The resulting fragment was then ligated into the Sal I-Bgl II sites of pSCT-025A and pSCT-029A creating pSCT-037 and pSCT-038 respectively (see FIG. 8)

Construction of pSCT-034 pSCT-034 is a trigenic expression plasmid containing three copies of the Tac-Lac-ompAsCTgly RRNB T1–T2 transcription cassette. This vector (see FIG. 9) was constructed by inserting the described cartridge from pCPM-01A into Sal I and Eco RI sites of pSCT-029A adding a third copy of the expression cartridge. The method of construction is identical to the method for the construction of pSCT-029A from pCPM-01A and pSCT-025A. The 3' Sal I and Eco RI sites are recreated, providing the sites necessary for adding more copies of the cartridge.

TABLE 1

| Cloning fragment | Component type | Origin or template |
| --- | --- | --- |
| pGEM 11 ZF(+) | Plasmid | Promega |
| pGEM 1N | Plasmid | Pharmacia Biosciences |
| pSP 72 | Plasmid | Promega |
| Tac promoter | tac promoter DNA block | Pharmacia Biosciences |
| pelB-sCTgly-cas2* | PCR amplified gene | pelB-sCTgly gene assembled from synthetic oligonucleotides |
| Kanamycin resistance gene | Gene block | Pharmacia Biosciences |
| RRNB T1–T2 | PCR fragment | Ribosomal protein gene T1 and T2 transcription terminators from pKK 233-2 |
| pSP72 T1–T2 | Subclone | Subcloned from above PCR fragment into pSP72 |
| Lac repressor (LAC-IQ) | PCR amplified gene | pGEX 1-N plasmid |
| Lac promoter/operator (P/O) | PCR amplified fragment | pGEM11ZF+ |
| lpp-lac-ompAsCTgly (partial) | PCR amplified product (3' PCR primer contains first 17 nucleotides of sCTgly) | pIN IIIA |
| pSP 72-ompA | Subclone of above fragment | Subcloned from above PCR fragment into pSP72 |
| lac-ompAsCTgly | PCR amplified operon | pSCT-019 |
| RRNB T-T2-02 | PCR amplified product | pSCT-025 |
| OMPASCTGLY T1–T2 CISTRON | PCR amplified product of ompAsCTgly subcloned into pSP72 T1–T2 | pSCT-025 (template) |
| SEC E | PCR amplified gene | E. coli WA 837 genomic DNA |
| PRLA-4 | PCR amplified gene | E. coli prlA 4 gene from vector pRLA41++ |
| TRP P/O | Assembled synthetic oligonucleotide gene | E. coli tryptophan E promoter/operator Sequence from literature |

*pelB - signal sequence of the pectate lyase B gene from Erwinia carotovora.
++The pRLA41 vector was provided by Tom Silhavy at Princeton University. The prlA-4 mutant allele may have properties that allow easier translocation of heterologous peptides and proteins. However, the natural prlA (secY) gene should function as well.

Transformation of E. coli BLR with DSCT-029A or PSCT-038

After constructing the pSCT-029A or pSCT-038 plasmids, i.e., ligation of the various DNA fragments, it is necessary to use the final ligation mixture to transform an E. coil host strain for propagation of the plasmid and for future protein expression work. To perform this transformation it is necessary to cause the E. coli cells to be competent to receive the DNA The preparation of competent cells can be done by a variety of methods such as $CaCl_2$ treatment and electroporation. For the final preparation of preferred cell lines, UGL 165 and UGL 703, we use both methods in series according to the following protocols.

I. Primary Transformation into the E. coli K-12 host, BB4

This first transformation is not essential, but is preferred because the E. coli BB4 K-12 host has a high transformation efficiency which results in a large number of transformants and a high probability of identifying a variety of desired clones.

A. Preparation of Competent BB4 Cells by $CaCl_2$ Treatment
BB4 Genotype . . . LE392.32 [F' $lacI^Q\Delta MI5proAB$ Tn 10 ($Tet^R$)]
1. Prepare an overnight saturated culture of the host cell.
2. Prepare a fresh host cell culture by inoculating 100 ml of medium to 0.5% (v/v) and grow to an $A_{600}$ nm of 0.02–0.03.
3. Grow the culture to an $A_{600}$ nm of 0.15–0.3, approximately 3 doublings.
4. Store the cells on ice for 10 minutes.
5. Remove the cells from the culture media by centrifugation, 5K rpm×10 min.
6. Resuspend the pelleted cells in 0.5 volumes of ice cold 0.1 M $CaCl_2$ store on ice for 30 minutes, then pellet the cells as previously described.
7. Resuspend the pelleted cells in 0.1× volume of 0.1 M $CaCl_2$; store on ice for 1 hour prior to use.

B. Transformation Protocol
1. To 100 ul of competent cells prepared as described add 1–2 ul of a ligation mixture which should ideally contain 2–10 ng of plasmid vector DNA.
2. Store the mixture on ice for 30 minutes.
3. Heat shock the mixture by placing in a heating block or water bath at 37° C.
4. Add to the mixture 1 ml of prewarmed culture medium and incubate the mixture at 37° C. for 30–60 minutes.
5. Spread an appropriate amount of transformation mixture onto an appropriate solid media containing the necessary selective antibiotic and incubate the plates 18–24 hours until colonies appear.

II. Secondary Transformation
Transformants are identified by a variety of methods. Several clones are chosen for transfer to the second host, E.

coli B host strain, BLR. BLR is the host strain of choice or fermentation and protein expression.

The genotype of BLR is F$^-$ ompT hsds$_B(r_B^- \cdot m_B^-)$ gal dcm Δ(srl-recA) 306::Tn10(Tc$^R$). E. coli cells will accept DNA after being exposed to an electric field under controlled and specified conditions. E. coli B host strains are more easily transformed with an intact plasmid, rather than a ligation mixture, and are more receptive to foreign DNA when made competent by electroporation than by CaCl$_2$ treatment.

A. Preparation of competent E. coli BLR cells for Subsequent Electroporation

1. Prepare an overnight saturated culture of the host cell.
2. Prepare a fresh host cell culture by inoculating 100 ml of medium to 1.0% (v/v) and grow to an A$_{600}$ nm of 0.3–0.5.
3. Harvest the cells by centrifugation after chilling the culture on ice for 15 min.
4. Decant the supernatant, removing as much media as possible. Resuspend the cells in a total volume of 100 mls of ice cold aqueous 10% glycerol, w/v (the glycerol should be of extra high quality). Re-centrifuge the resuspended cells immediately.
5. Resuspend the cells in 50 mls of ice cold 10% glycerol (w/v). Re-centrifuge.
6. Resuspend the cells in 25 mls of ice cold 10% glycerol (w/v). Re-centrifuge.
7. Repeat step 6.
8. Resuspend the cells in a final volume of 2 mls of ice cold 10% glycerol (w/v). The final cell concentration should be 1–3×10$^{10}$ cells/mi. The cells can be stored for up to 1 year at −80° C.

B. Transformation by Electroporation

1. Incubate sterile cuvettes and the white chamber slide for 10 min on ice. Also incubate several polypropylene tubes on ice.
2. Mix 40 ul of cell suspension with 1–2 μl of solution containing plasmid DNA in Tris/EDTA at an approximate concentration of 100 pg/μl. (The DNA mixture must be as salt free as possible to prevent arcing of the equipment.) Mix the solution well and incubate on ice for 0.5–1.0 min.
3. Set the Gene-Pulser apparatus at 25 uF. Set the pulse controller resistance at 200 ohms. Set the Gene-Pulser apparatus to 2.5 Kv with 0.2 cm cuvettes or 1.5–1.8 Kv when using 1.0 cm cuvettes.

Transfer the mixture of cells and DNA to a cold electroporation cuvette and shake the suspension to the bottom of the cuvette removing all of the air bubbles. Place the cuvette in the chilled safety chamber slide and push the slide into the chamber until the cuvette is seated between the contacts in the base of the chamber.
4. Pulse the cuvette once at above setting.
5. Immediately add 1 ml of SOC (20 g Tryptone, 5 g yeast extract, 0.5 g NaCl, 1L H$_2$O and 20 mM glucose) buffered media to the cuvette, resuspend the cells.
6. Transfer the suspension to a sterile 17×100 mm polypropylene tube and incubate at 37° C. for 1 hour.
7. Plate the electroporated mixture on selective media plates.

Production of sCTclv (Fermentation)

Fermentation batch media is prepared using the components listed in Table 2. The fermentation is inoculated with a late log phase culture grown in inoculation media (Table 2). The inoculation volume is determined by the amount of inoculum (number of cells) needed to reach an initial A 600 nm within the fermenter between 0.015 and 0.24. The pH, DO$_2$, and temperature parameters for the fermentation run are listed in Table 3. The fed batch state of the fermentation is started when the glycerol in the batch media is depleted. [Glycerol depletion can be determined by a spike in dissolved oxygen and/or a glycerol assay.] The feed rate is set to maintain a constant cell division rate based on cell mass (dry cell weight) at the time of glycerol depletion. Feed components are listed in Table 2. The feed rate is based on the following formula:

$$Q = \frac{(V) \times (MU) \times (dcw) \times (e^{Mu+t})}{(Yx/sx[Feed])}$$

where:

Mu=growth rate (in doublings per hour)

dcw=dry cell weight in grams per liter of medium at feed start determined empirically for individual E. coli strains t=time in hours Y x/s=glycerol utilization constant for host (0.327 for E. coli WA 837; similar for BLR)

v=fermentation volume in liters

[feed]=grams glycerol per liter of feed medium (629 grams per liter used in all examples reported herein).

Q=glycerol feed rate, liters/hour

The induction process is accomplished using a gradient induction coupled to the feed rate increasing the inducer (IPTG) over time matching the set growth rate.

The fermentation in progress is monitored by measuring absorbance at 600 nm, wet cell weight in g/l, in addition to CEX chromatography analysis of media samples for the presence and concentration of sCTgly in mg/l.

Glycine can be added to the fermentation in order to increase outer membrane permeability Glycine can be added to the batch media or to the feed. Preferably the glycine is added to the feed so that the glycine concentration in the fermentation culture increases with the rate of cell growth. The optimal concentration of glycine should be in the range of 0.1–1 grams per 100 ml at the final time point of the fermentation. In practice, the amount of glycine added to the feed is calculated so that the desired glycine concentration at the fermentation end is achieved. The actual amount of glycine added is dependent on the length of the fermentation in time, post induction, and final glycine concentration desired. The methods we have used: 24 g/l of glycine was added to the fermentation feed, which results in a final glycine concentration of 5 g/l at 26 hours post induction. We have found that adding glycine to the feed is more effective than adding glycine to the batch media.

TABLE 2

| Media Component List: | |
|---|---|
| Components | Quantity g/L |
| Inoculation Media | |
| (NH$_4$)$_2$SO$_4$ | 7.00 |
| KH$_2$PO$_4$ | 2.00 |
| MgSO$_4$-7H$_2$O | 1.00 |
| CaCl$_2$ | 0.25 |
| FeSO$_4$-7H$_2$O | 0.05 |
| Sodium Citrate | 1.50 |

TABLE 2-continued

Media Component List:

| Components | Quantity g/L |
|---|---|
| N-Z Case+ | 5.00 |
| Hy Yest 412 | 2.00 |
| L-Methionine | 4.50 |
| Kanamycin | 0.05 |
| Glycerol | 18.00 |
| Batch Media | |
| $(NH_4)_2SO_4$ | 14.80 |
| $KH_2PO_4$ | 4.40 |
| $MgSO_4\text{-}7H_2O$ | 2.10 |
| $CaCl_2$ | 0.53 |
| $FeSO_4\text{-}7H_2O$ | 0.11 |
| Sodium Citrate | 2.20 |
| N-Z Case+ | 10.60 |
| Hy Yest 412 | 3.10 |
| L-Methionine | 4.50 |
| Kanamycin | 0.05 |
| Glycerol | 2.50 |
| Feed Media | |
| Glycerol | 629 |
| IPTG | 2.80 |

TABLE 3

Conditions determined for fermentation parameters

| Parameter | Most Preferred | Preferred | Good |
|---|---|---|---|
| pH | 6.78–6.85 | 6.50–7.00 | 6.00–7.5 |
| Temp ° C. | 29.5–30.5 | 28.0–32.0 | 20.0–35.0 |
| DO (oxygen saturation) | >80% | >70% | >50% |
| Mu value | 0.12–0.14 | 0.10–0.16 | 0.05–0.20 |
| Fermentation Time (Hours post induction) | 24–27 | 22–29 | 20–32 |

Isolation of sCTaly

The conditioned medium is harvested by separating the cells from medium using either Tangential Flow Filtration or centrifugation to collect the media, and discarding the cells. The excreted sCTgly is stabilized in the media by adding 2.0 N HCl to a final pH of 3.0. The glycine-extended salmon calcitonin is stable for extended periods of time at pH 3.0. After cell removal and pH stabilization, the peptide is purified using cation exchange and reverse-phase chromatography methods. While reverse phase chromatography followed by cation exchange chromatography can provide good purification, it is preferred that an initial cation exchange step also be included prior to the reverse phase liquid chromatography. For large purification, this reduces the volume to be subjected to reverse phase chromatography, thus reducing environmental and safety concerns raised by the necessity of using high volumes of organic solvents such as acetonitrile.

Another preferred modification is S-sulfonation of the cysteine residues of the salmon calcitonin peptide prior to or during purification in order to improve yields of the monomeric peptide.

Description of Clones

The monogenic UGL 172 clone is an *E. coli* BLR host strain containing vector pSCT-025A which comprises one transcription cassette (monogenic) coding for salmon calcitonin with a C-terminal glycine (sCTgly).[2] The digenic UGL 165 clone is an *E. coli* BLR host strain containing vector pSCT-029A which comprises two cassettes in tandem (digenic) each coding for salmon calcitonin with a C-terminal glycine (sCTgly). The trigenic UGL 168 clone is an *E. coli* BLR strain containing vector pSCT-034 which comprises three cassettes in tandem (trigenic) each coding for salmon calcitonin with a C-terminal glycine (sCTgly). The monogenic UGL 702 clone is an *E. coli* BLR strain containing vector pSCT-037 which comprises 1 cassette and secretion factor genes. The digenic UGL 703 clone is an *E. coli* BLR strain containing vector pSCT-038 which comprises 2 cassettes in tandem and secretion factor genes.

[2] A preferred transcription cassette contains the dual tac/lac promoter followed by a ribosome binding site followed by sequences for the OmpA signal peptide followed by sequences for sCTgly followed by transcription terminator sequences rrnB T1–T2.

EXAMPLE 1

UGL 165 Fermentation at 1L Scale

The fermentation of the UGL 165 clone was carried out as described under Experimental details. Table 4 summarizes the fermentation parameters and results. Briefly, UGL 165 clonal cells were grown in inoculation medium and used to seed a fermenter containing 1 liter of batch medium to give an initial $A_{600}$ nm of 0.06. Cells were grown for 6.25 hours until the glycerol in the medium was depleted. Then, the fed batch stage of the fermentation was started and supplemented continuously with the feed medium for 25.5 hours. The conditions at time zero (beginning of feed and induction) were as follows: oxygen saturation, 94%; temperature 30° C.; and pH 6.8. The conditions at the end of fermentation (time 25.5 hours) were as follows: oxygen saturation, 40%; temperature 31° C.; and pH 6.8. Also, at the end of fermentation, the absorbance at 600 nm was equal to 113.3 and the wet cell weight in g per liter was 168 g. The sCTgly production at the end of fermentation was also measured to be 222 mg/liter of medium (see FIG. 10 and table 4).

TABLE 4

Fermentation Summary of UGL 165

| Time point Hrs. Post Feed | $A_{600}$ nm | wet cell weight g/L | sCT gly mg/L ** | Feed vol added, mls | [IPTG] uM | Agitation RPM |
|---|---|---|---|---|---|---|
| −6.25 | 0.06 | — | — | — | — | 500 |
| 0*** | 11.1 | — | — | — | — | 1300 |
| 15 | 51.7 | 83.3 | not assayed | 44.1 | 528 | 1000 |
| 17 | 48.7 | 92.3 | not assayed | 51.3 | 614 | 1200 |
| 19 | 53.6 | 100.5 | 38 | 78.2 | 948 | 1300 |
| 21 | 67.6 | 117.3 | 77 | 104.8 | 1256 | 1300 |
| 22 | 86.7 | 130.9 | 111 | 120.4 | 1442 | 1350 |
| 23 | 92.6 | 140.0 | 104 | 138.2 | 1654 | 1350 |
| 24 | 106.5 | 153.7 | 156 | 158.4 | 1896 | 1350 |
| 25 | 108.5 | 162.8 | 183 | 181.2 | 2174 | 1400 |
| 25.5 | 113.3 | 168 | 222 | 194.1 | 2324 | 1400 |

**sCTgly determined using the CEX-HPLC assay as described in Example 4.
***Agitation turned to 1450 rpm overnight @ 2 hrs post start feed

EXAMPLE 2

UGL 703 Fermentation at 1L Scale

Recombinant *E. coli* UGL 703 has been deposited with the American Type Culture Collection (ATCC) as ATCC 98395 in accordance with the provision of the Budapest Treaty relating to the deposit of microorganisms for purposes of patent procedure. The fermentation of the UGL 703 clone was carried out as described under Experimental details. Table 5 summarizes the conditions of this fermentation. Briefly, UGL 703 clone was grown in inoculation medium and used to seed a fermenter containing 1 liter batch medium to give an initial $A_{600}$ nm of 0.06 (preference is 0.06 to 0.12). Cells were grown for 6.25 hours (preferred range is from 6.0 to 7.0 hours) until the glycerol in the medium was depleted. Then, the fed batch stage of the fermentation was started and supplemented continuously with the feed medium for 26 hours. The conditions at time zero (beginning of feed and induction) were as follows: oxygen saturation, 95%; temperature 30° C.; and pH 6.8. The conditions at the end of fermentation (time 26 hours) were as follows: oxygen saturation, 80%; temperature 31° C.; and pH 6.8. Also, at the end of fermentation, the absorbance at 600 nm was equal to 80.9 and the wet cell weight in grams per liter was 129.1. The sCTgly production was also measured to be 234 mg/liter of medium (see FIG. 11 and table 5).

TABLE 5

Fermentation Summary of UGL 703

| Time point | A 600 | wet cell weight g/L | sCT gly mg/L ** | Feed vol added, mls | [IPTG] uM | Agitation RPM |
|---|---|---|---|---|---|---|
| −6.5 | 0.06 | — | — | — | — | 500 |
| 0 | 8.1 | — | — | — | — | 1300 |
| 15.5 | 22.6 | 7.3 | ~18 | 47.5 | 570 | 1150 |
| 19 | 36.5 | 83.1 | 25 | 72.9 | 948 | 1250 |
| 21 | 53.5 | 94.2 | 53 | 104.8 | 1256 | 1350 |
| 22 | 61.3 | 100.8 | 58 | 120.4 | 1442 | 1450 |
| 23 | 59.7 | 106.0 | 69 | 138.2 | 1654 | 1550 |
| 24 | 73.3 | 119.0 | 83 | 158.4 | 1898 | 1580 |
| 25 | 74.1 | 119.1 | 203 | 181.1 | 2174 | 1620 |
| 26 | 80.9 | 129.1 | 284 | 207.6 | 2487 | 1620 |

**sCTgly determined using the CEX-HPLC assay as described in Example 4.

Conclusions

Other experiments were carried out under similar overall conditions using UGL 172, UGL 168 and UGL 702 clones. FIGS. 12 and 13 indicate that the digenic UGL 165 clone is best suited for production of sCTgly with the trigenic UGL 165 clone being second best over the monogenic UGL 173 clone. However, the production of sCTgly by UGL 165 can still be improved in the presence of co-expressed secretion factors (UGL 703) (compare FIGS. 10 and 11 and 17).

With regard to oxygen saturation during fermentation, FIGS. 14A and 14B support the conclusion that added oxygen in the fermentation medium is not critical to cell growth of UGL 165 but is very important in increasing the production of sCTgly.

FIGS. 15A, 15B, and 16 clearly indicate that the *E. coli* strain BLR is best suited for production of sCTgly.

The production of sCTgly can be still further increased by the addition of glycine as an added feed component.

EXAMPLE 3

Purification of sCTqlV from UGL 165 Culture Media:
Cation-Exchange Chromatography #1:

Approximately 1000 L of culture media which had been harvested by either tangential flow filtration or centrifugation was acidified with a sufficient volume of 2N hydrochloric acid to decrease the pH to 3.0. The media was subsequently diluted with a sufficient volume of water to decrease the conductivity to ≦7.5 mS. The diluted media was loaded onto a cation-exchange column (Pharmacia SP-Sepharose Big Beads, 99.0 cm×13.0 cm) which had been equilibrated with 10 mM citric acid pH 3.0 at a flow rate of 25 L/min. (3.25 cm/min.). After the loading was complete, the column was washed with 10 mM citric acid pH 3.0 at 8 L/min (1.0 cm/min) for approximately 40 minutes (3 bed volumes) or until a stable UV baseline was achieved. The product (sCTgly) was eluted with 10 mM citric acid, 350 mM sodium chloride pH 3.0 at a flow rate of 8 L/min. (1.0 cm/min.). The column was cleaned and sanitized with 0.5 M sodium hydroxide. 1.0 M sodium chloride for 60.0 minutes (5.0 bed volumes) at 8 L/min. (1.0 cm/min).

To a stirred tank containing the resulting CEX#1 eluate (approximately 100 L) is added 60.57 grams of tromethamine. The solution is stirred until all solids are dissolved. The pH of the solution is adjusted to 8.25 [range: 8.0 to 8.5] using 2 M NaOH. 23.64 grams of TRIS.HCl (Tris[hydroxymethyl]amlnomethane hydrochloride) is added and the solution is stirred until all solids are dissolved. A solution of 1.0 kg of sodium sulfite dissolved in TRIS.HCl and a solution of 200 grams of sodium tetrathionate dissolved in TRIS.HCl are added to the tank with stirring. The reaction is allowed to stir for 15 minutes. If necessary, the pH is adjusted to 8.25 [range: 8.0 to 8.5] with 2 M NaOH. The reaction mixture is stirred overnight at room temperature. The pH of the reaction mixture is adjusted to 2.25 [range: 2.0 to 2.5] with 2 M HCl.

Reverse-phase Chromatography #1 (RP #1):

The resulting S-sulfonation reaction mixture (approximately 100 L) was loaded directly onto a reverse-phase column (Toso Haas Amberchrom CG300md, 25.0 cm×18.0 cm) which had been equilibrated with 0.1% trifluoroacetic acid at 2.0 L/min. (4.0 cm/min). After loading was complete, the column was washed with 0.1% trifluoroacetic acid at 750 ml/min. (1.5 cm/min.) until a stable UV baseline was achieved. The column was washed with 0.1% trifluoroacetic acid, 20% acetonitrile at 750 ml/min. (1.5 cm/min.) until the principal contaminant peak completely eluted. The product (sCTgly) was eluted with 0.1% trifluoroacetic acid, 40% acetonitrile at 750 ml/min. (1.5 cm/min.). The column was cleaned with 0.1% trifluoroacetic acid, 80% acetonitrile for 30 minutes at 750 ml/min. (1.5 cm/min.).

Cation-exchange Chromatography #2 (CEX #2):

The resulting RP #1 eluate (approximately 8.0 L) was loaded directly onto a cation-exchange column (E. Merck Fractogel EMD SO3 650M, 18.0 cm×24.0 cm) which had been equilibrated with 25 mM MES (2-[N-morpholino]-ethanesulfonic acid) pH 5.8 at 500 ml/min. (2.0 cm/min.). After the loading was complete, the column was washed at 750 ml/min. (3.0 cm/min.) with 25 mM MES (2-[N-morpholino]-ethanesulfonic acid) pH 5.8 until the column effluent returned to pH 5.8 (range 5.6–5.9). The column was washed with 25 mM MES (2-[N-morpholino]-ethanesulfonic acid), pH 5.8 for an additional 30 minutes at 750 ml/min. (3.0 m/min.) to remove the principal peptide contaminants. The product (sCTgly) was eluted with 25 EM MES, 100 mM sodium chloride pH 5.8 at 750 ml/min. (3.0-cm/min.). The product fraction is adjusted to pH 3.0–5.0 with 1.0 M HCl unless amidation follows immediately. The column was cleaned and sanitized with 0.1 M sodium hydroxide, 1.0 M sodium chloride for 60 minutes at 750 ml/min. (3.0 m/min.).

Amidation Reaction.

The resulting pH-adjusted CEX #2 eluate contains purified sCTgly which is a suitable substrate solution for use in the in vitro conversion of sCTgly to authentic salmon calcitonin, a reaction catalyzed by peptidyl glycine α-amidating enzyme (PAM) as shown below in Example 5.

EXAMPLE 4

Analytical Cation-exchange HPLC for quantification of sCTgrly:

sCTgly in collected chromatography fractions was identified and quantified by analytical CEX-HPLC. An aliquot of each fraction was loaded onto a cation-exchange column (The Nest Group, Polysulfoethyl aspartamide, 4.6 mm×50 mm) which had been equilibrated with 10 mM sodium phosphate pH 5.0 at a flow rate of 1.2 ml/min. Separation was achieved by performing a linear gradient from 10 mM sodium phosphate pH 5.0 to 10 mM sodium phosphate, 250 mM sodium chloride pH 5.0 at 1.2 ml/min over 15 minutes. The column effluent was monitored by UV absorbance at 220 nm. sCTgly was identified by comparison of its retention time to that of a purified sCTgly reference standard. sCTgly was quantified by peak area as compared to the sCTgly reference standard. This analytical method was also used to quantify SCTgly from the fermentation medium.

EXAMPLE 5

Conversion of Glycine-extended Salmon Calcitonin to Authentic Salmon Calcitonin Using α-amidatinq Enzyme In order to obtain the optimal yields of amidated salmon calcitonin, the following critical parameters are observed:

1) The amidation reaction is carried out in a silanized glass vessel to prevent non-specific adsorption of peptide to the reaction vessel.
2) A high level of dissolved oxygen is maintained in the reaction mixture by sparging and/or agitation. Preferably, the level of dissolved oxygen is ≧75%.
3) Incubation temperature during amidation is maintained between 35° C.–39° C.
4) The pH of the amidation reaction is maintained between 6.0 and 6.5.
5) The starting concentration of glycine-extended salmon calcitonin in the amidation reaction should be between 3.5–10.5 mg/ml (0.95 mM to 2.9 mM).
6) When 12,000–24,000 units/ml of substantially protease-free α-amidating enzyme (peptidyl glycine α-amidating monooxygenase, herein referred to as "PAM") are added to the reaction mixture and the concentration of substrate is as indicated in 5) above, the reaction is allowed to proceed for 4–6 hours. However, the reaction time can be further increased up to 24 hours without deleterious effects to the product.
7) To prevent the amidation reaction from becoming ascorbate limiting, an additional equivalent of ascorbate is added at about the midpoint of the reaction.

The components of the amidation reaction mixture are the following:

3.5–10.5 mg/ml of S-sulfonated, glycine extended salmon calcitonin 30 mM MES buffer, pH 6.0–6.5

0.5 to 1.0 uM $CUSO_4$ (e.g. 0.5)

4–15 mM KI (e.g. 5)

1–5% Ethanol (e.g. 1%)

10–100 ug/ml Catalase (e.g 35)

1.5–3.0 mM Ascorbate (e.g. 1.5)

peptidyl glycine α-amidating monooxygenase (12,000–24,000 units per ml of reaction mixture. 1 unit is 1 picomole per minute conversion of DansylTyr-Val-Gly substrate to product at 37° C. at pH 7). The PAM enzyme may be obtained as described in Miller et al., ABB 298: 380–388 (1992) U.S. Pat. No. 4,708,934, European publication 0 308 067 and 0 382 403, and Biotechnology Vol. II (1993) pp. 64–70, the disclosures of which are hereby incorporated by reference.

The glycine extended salmon calcitonin may be produced by the fermentation as described in Example 1 or Example 2 and purified as described in Example 3 prior to amidation.

In instances where the enzyme used for amidation is peptidyl glycine α-hydroxylating monooxygenase (PHM), the same reaction mixture is used as that described above, substituting PHM for PAM. In addition, at the end of the 4 to 6 hour incubation period, the pH of the reaction mixture is increased by the addition of base to between 8 and 9. The reaction mixture is agitated for an additional 4 to 8 hours prior to terminating the reaction. Peptidyl glycine α-hydroxylating monooxygenase may be obtained by expressing only the N-terminal portion of PAM (about the first 40 dKa). See e.g. Mizuno et al. BBRC Vol. 148, No. 2, pp. 546–52 (1987) the disclosure of which (as it relates to Mizuno's "AE 1" is incorporated herein by reference. Frog skin is known to express PHM naturally.

After the amidation reaction has been terminated, the reaction is diluted with sufficient water to bring the final peptide concentration to less than 3.0 mg/ml. Sufficient 1 M TRIS pH 9.0 is added to the mixture to bring the final concentration of TRIS to approximately 100 mM. If necessary, the pH is adjusted to [8.0 to 9.0] with 2 M NaOH. A 3.0 fold excess of L-cysteine, over the final concentration (mM) of $SO_3$-sCT, is added slowly with stirring to the reaction mixture. If necessary, the pH is adjusted to [8.0 to 8.5] with 2 M NaOH. The renaturation reaction is stirred for 1 hour at room temperature. The reaction is terminated by acidification with 10% phosphoric acid to pH 2.0 [1.9 to 2.3].

EXAMPLE 6

Post-amidation Purification

Cation Exchange Chromatography #3 (CEX #3):

This column is used to purify sCT following α-amidation and renaturation. The principal contaminant following α-amidation/renaturation is ScTG. CEX #3 chromatography employs an Amicon Vantage-A column (18.0×16.0 cm) packed with Toyopearl SP650S resin. The unit operation is accomplished using water for injection (WFI) and solutions of 0.5 M, 50 mM and 175 mM sodium chloride along with 150 mM sodium phosphate pH 5.5. A brief description of the process steps follows:

1) The operational flow rate is set to 750 ml/min.
2) The following parameters which are used to monitor the chromatography are set using LC system controller:

UV wavelength 230 nm

Range 0.64 AUFS

Conductivity X1000

3) The column is initially washed with WFI for at least 5 minutes at a flow rate of 750 ml/min.
4) The dilution pump (150 mM sodium phosphate pH 5.0) is set to 50 ml/min. and the column is equilibrated with 10 mM sodium phosphate at a flow rate of 750 ml/min until a stable pH baseline is observed.
5) The column is re-equilibrated with 10 mM sodium phosphate at a flow rate of 750 ml/min until a stable pH baseline below 6.0 is achieved. (Note: If the pH of the column is not below 6.0 then a 150 mM sodium phosphate wash is required.) If the 150 mM sodium phosphate pH 5.5 wash is performed the column must be re-equilibrated using 10 mM sodium phosphate pH 5.5 before proceeding at the next step.

6) Following the re-equilibration, the column is subjected to a blank elution with 175 mM sodium chloride; 10 mM sodium phosphate pH 5.5 for 4 minutes at a flow rate of 750 ml/min.

7) The column is re-equilibrated with 10 mM sodium phosphate pH 5.5 at a flow rate of 750 ml/min until a stable pH baseline is achieved.

8) Once equilibration is achieved the amidated/renatured output containing 10–25 gram of sCT is pH adjusted to 3.5 using 2 N sodium hydroxide and loaded onto the CEX #3 column at 400 ml/min. The sample load is chased by rinsing the load container with 500 ml of WFI.

9) Following the load the column is washed with 10 mM sodium phosphate pH 5.5 at a flow rate of 750 ml/min. for 30 minutes or until the pH of the column stabilizes above 5.0.

10) Once the pH of the column has stabilized above 5.0 the column is washed, at 750 ml/min., with 50 mm sodium chloride; 10 mm sodium phosphate pH 5.5 for 100 minutes or until the sCTgly peak emerges.

11) Once the 100 minutes has expired the 175 mm sodium chloride is attached to the system. The column is washed with 175 mM sodium chloride; 10 mM sodium phosphate pH 5.5 at a flow rate of 750 ml/min. and the product eluted. The entire product peak is collected in one container. The weight of the CEX3 output material is determined and 1 N acetic acid (10% fraction weight) is added to the fraction.

12) The column is stripped with 0.5 M sodium chloride; 10 mM sodium phosphate pH 5.5 at a flow rate of 750 ml/min. for 15 minutes.

13) Once the column has been stripped with 1.0 M sodium chloride/0.25 N sodium hydroxide is attached to the system. The dilution pump is set to 0.000 ml/min. and the column washed with 1.0 M sodium chloride/0.25 N sodium hydroxide at a flow rate of 600 ml/min. for at least 30 minutes.

14) The column is washed with WFI for 5 minutes at a flow rate of 750 ml/min.

15) The column is washed with 10 mM sodium hydroxide at a flow rate of 500 ml/min. for at 30 minutes. The column is stored under these conditions.

Reverse-phase Chromatography (RP #2):

This step follows CEX #3 and is used as a salt and buffer exchange step prior to lyophilization. The main objective of the step is to exchange the salt with acetate. RP #2 chromatography employs an Amicon Vantage-A column (13.0× 12.5 cm) packed with Amberchrom CG300md resin. The unit operation is accomplished using water for injection, ethyl alcohol, 250 mM sodium acetate and 0.5% acetic acid. A brief description of the process steps follows:

1) The CEX #3 eluate (approximately 4 liters) is acidified to pH 2.0 with phosphoric acid and then diluted with 3 equal volumes of 333 mM sodium acetate solution, and allowed to stand for at least 1 hour.

2) The flow rate is set to 320 ml/min. while the dilution pump (0.5% acetic acid) is set to 80 ml/min. for an overall operational flow rate of 400 ml/min.

3) The following parameters which are used to monitor the chromatography are set using LC system controller:
UV wavelength 230 nm
Range 2.54 AUFS
Conductivity X 1000

4) The column is initially washed with 0.1% is acetic acid at a flow rate of 400 ml/min. until a stable conductivity baseline is observed.

5) The column is stripped with 80% ethyl alcohol, 0.1% acetic acid at a flow rate of 400 ml/min. until a stable pH baseline is observed.

6) The column is washed with 0.1% acetic acid until a stable pH baseline is observed.

7) Following the wash, a column test is performed to track resin cleaning. The column is subjected to a blank elution with 40% ethyl alcohol; 0.1% acetic acid for 6 minutes at a flow rate of 400 ml/min. The collected eluate from the column test is submitted at QC for analytical testing.

8) The column is washed with 0.1% acetic acid at a flow rate of 400 ml/min until a stable conductivity baseline is observed.

9) Upon completion of the wash, the WFI is disconnected from the inlet and the 250 mM sodium acetate is connector. The dilution pump is set to 0.000 ml/min. The column is equilibrated with 250 mM sodium acetate at a flow rate of 400 ml/min. until a stable pH baseline is observed.

10) Once equilibration is achieved, the CEX #3 eluate is loaded onto the RP #2 column at 400 ml/min. The sample load is chased by rinsing the load container with 1.0 liters of 250 mM sodium acetate.

11) The column is washed using 250 mM sodium acetate at a flow rate of 400 ml/min. for 60 minutes.

12) Following the sodium acetate wash, the sodium acetate is disconnected from the inlet and the WFI is connected. The dilution pump is returned to a flow rate of 80 ml/min. and the column is washed with 0.1% acetic acid at a flow rate of 400 ml/min for 25 minutes.

13) Following the 0.1% acetic acid wash, the product is eluted using 40% ethyl alcohol; 0.1% acetic acid at a flow rate of 400 ml/min. The entire product peak is collected, and subjected to lyophilization to yield purified sCT powder.

14) The column is stripped with 80% ethyl alcohol; 0.1% acetic acid at a flow rate of 400 ml/min. for at least 20 minutes.

15) Following the strip, the dilution pump is set to 0.000 ml/min. and the column is washed with WFI at a flow rate of 400 ml/min. for at least 5 minutes.

16) After the WFI wash, the WFI is disconnected from the inlet and the 0.5N sodium hydroxide is connected. The column is washed with the 0.5N sodium hydroxide at a flow rate of 400 ml/min. for at least 20 minutes.

17) The 0.5N sodium hydroxide is disconnected from the system and the WFI is connected. The column is washed with 50% ethyl alcohol at a flow rate of 400 ml/min for at least 20 minutes The column is stored under these conditions.

18) The RP #3 eluate is stored at 2 to 8° C.

Although the present invention has been described in relation to particular embodiments thereof, many other variations and modifications and other uses will become apparent to those skilled in the art. The present invention therefore is not limited by the specific disclosure herein, but only by the appended claims.

What is claimed is:

1. An expression vector comprising:
(a) a coding region with nucleic acids coding for a peptide product coupled in reading frame 3' of nucleic acids coding for a signal peptide;

(b) a control region linked operably with the coding region, said control region comprising a plurality of promoters and at least one ribosome binding site, wherein at least one of said promoters is tac; and (c) nucleic acids coding for a repressor peptide capable of repressing expression controlled by at least one of said promoters, wherein said vector comprises a plurality of transcription cassettes, each cassette having said control region and said coding region.

2. The vector of claim 1, wherein the nucleic acids coding for the repressor encode a lac repressor.

* * * * *